| United States Patent [19] | [11] Patent Number: 5,700,785 |
| Suhadolnik et al. | [45] Date of Patent: Dec. 23, 1997 |

[54] 3'-DEOXY OR 3'-O-SUBSTITUTED-2',5'-OLIGOADENYLATES AS ANTIVIRAL AGENTS

[75] Inventors: Robert J. Suhadolnik, Roslyn, Pa.; Wolfgang Pfleiderer, Constance, Germany

[73] Assignee: Temple University - Of The Commonwealth System of Higher Education, Philadelphia, Pa.

[21] Appl. No.: 210,406

[22] Filed: Mar. 14, 1994

Related U.S. Application Data

[63] Continuation of Ser. No. 964,111, Oct. 20, 1992, abandoned, which is a continuation of Ser. No. 613,848, filed as PCT/US89/02284, May 24, 1989, abandoned, which is a continuation-in-part of Ser. No. 204,659, Jun. 9, 1988, abandoned, which is a continuation-in-part of Ser. No. 144,602, Jan. 11, 1988, Pat. No. 4,859,768, which is a continuation of Ser. No. 629,660, Jul. 11, 1984, abandoned.

[51] Int. Cl.$^6$ ........................... A61K 31/70; C07H 21/02
[52] U.S. Cl. ........................... 514/44; 536/25.6; 536/25.2; 514/47
[58] Field of Search ........................... 514/44, 47; 536/25.2, 536/25.6

[56] References Cited

U.S. PATENT DOCUMENTS

| 4,210,746 | 7/1980 | Kerr et al. | 536/25.2 |
| 4,464,359 | 8/1984 | Suhadolnik et al. | 514/47 |
| 4,539,313 | 9/1985 | Suhadolnik et al. | 514/47 |
| 4,654,326 | 3/1987 | Devash et al. | 514/47 |
| 4,824,941 | 4/1989 | Gordon et al. | 530/403 |
| 4,855,304 | 8/1989 | Devash | 514/47 |
| 4,859,768 | 8/1989 | Suhadolnik et al. | 536/25.2 |
| 4,981,957 | 1/1991 | Lebleu et al. | 536/25.2 |

OTHER PUBLICATIONS

Liu et al., "Inhibition of Viral Reverse Transcriptase by 2',5'-Oligodenylates," *Biochem. Biophys. Res. Comm*, 145(1), 291–297(1987).

Henderson et al., "Inhibition of Epstein–Barr Virus–Associates Nuclear Antigen (EBNA) Induction by (2',5')–Oligoadenylates and the Cordecypin Analog: Mechanism of Action for Inhibition by EBV–Induced Transformation," *Virology*, 122(1), 198–201 (1982).

Lee et al., "Inhibition of Protein Synthesis by the Cordycepin Analog of (2'-5')ppp(Ap)$_n$A, (2', 5')ppp(3'dAp)$_n$3'dA, in Intact Mammalian Cells," *FEBS Letters*, 157, 205–209 (1983).

Suhadolnik et al. (IV), "Analogs of 2',5'–Oligoadenylates: Biological Probes for the Antiviral/Antitumor State of Mammalian Cells," *Nucleosides, Nucleotides and Their Biological Applications*, pp. 147–149, Nov. 1983.

Chapekar et al., "Cordycepin Analog of (A2'p)$_2$A: Evidence That It Functions as a Prodrug of Cordycepin," *Biochem. Biophys. Res. Comm.*, 115, 137–143 (1983).

Eppstein et al., "Mechanism of Antiviral Activity of (XyloA2'p)$_2$XyloA," *Virology*, 131, 341–354 (1983).

Eppstein et al. (II), "Analogs of (A2'p)$_n$A," *J. Biol. Chem.*, 257, 13390–13397 (1982).

Hughes et al., "2',5'–Oligoadenylates and Related 2',5'–Oligonucleotide Analogues. 2. Effect of Cellular Proliferation, Protein Synthesis, and Endoribonuclease Activity," *Biochemistry*, 22, 2127–2135 (1983).

Sharma et al., "3'–O–Methylated Analogs of 2–5A as Inhibitors of Virus Replication," *FEBS Letters*, 158, 298–300 (1983).

Engels et al., "Synthesis of 2'–End Modified 2',5'–Adenylate Trimers," *Tett. Lett.*, 21, 4339–4342 (1980).

Charubala et al., "Synthesis of Inosinate Trimer I2'p5'I2'p5'I and Tetramer I2'p5'I2'pI2'p5'I2," *Tett. Lett.*, 23, 4789–4792 (1982).

Haugh et al., "Analogues and Analogue Inhibitors of ppp(A2'p)$_n$A, Their Stability and Biological Activity," *Eur. J. Biochem.*, 132, 77–84 (1983).

Justesen et al., "Elongation Mechanism and Substrate Specificity of 2',5'–Oligoadenylate Synthetase," *Proc. Nat. Acad. Sci. USA*, 77, 4618–4622 (1980).

Baglioni et al., "Analogs of (2'–5')OligoA," *J. Biol. Chem.*, 256, 3253–3257 (1981).

Torrence et al., "Only One 3'–Hydroxyl Group of ppp5'A2'p5'A2'p5'A(2–5)A Is Required for Activation of the 2–5A–Dependent Endonuclease," *Biochem. Biophys. Res. Comm.*, 145, 291–297 (1987).

Sobol et al., "Human Immunodeficiency Virus Reverse Transcriptase: Inhibition by Structurally and Sterochemically Modified Analogs of 2–5A," *FASEB Journal*, 2, A830, Abstr. #3102 (1988).

Suhadolnik et al., "Inhibition of HIV–7 Reverse Transcriptase . . . ," Abst. #3582, IV International Conference on AIDS, Jun. 12, 1988.

Gura, "Antisense Has Growing Pains—Efforts to Develop Antisense Compounds as Therapies for Cancer, AIDS, and Other Diseases Have Encountered Some Unexpected Questions About How the Drugs Really Work," *Science*, 270, 575–577 (1995).

Visser et al., "Synthesis of some modified 2'–5'–linked oligoriboadenylates of 2–5A core" *Recl. Trav. Chim. Pay–Bas* 105, 85–91 (1986).

*Primary Examiner*—John Kight
*Assistant Examiner*—L. Eric Crane
*Attorney, Agent, or Firm*—Seidel, Gonda, Lavorgna & Monaco, P.C.

[57] ABSTRACT

Synthetic analogs of 2',5'-oligoadenylate wherein the aglycon, ribosyl moiety and/or terminal nucleoside have been modified are effective therapeutic agents, particularly against HIV infection. The analogs are utilized in compositions and methods for the treatment of disorders characterized by 2–5A pathway defects.

37 Claims, 3 Drawing Sheets

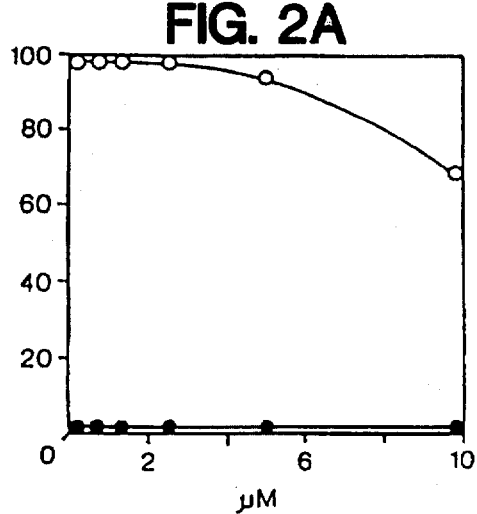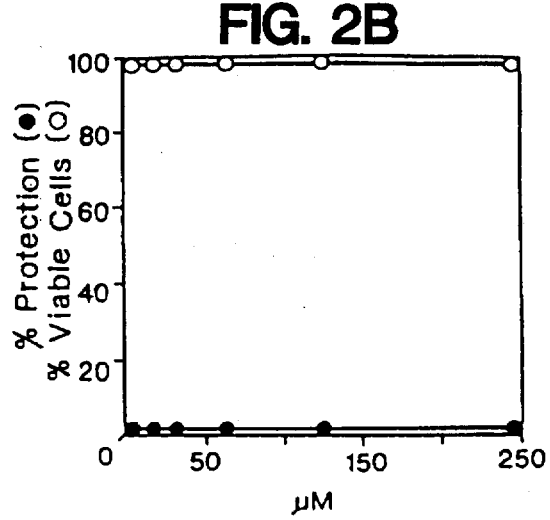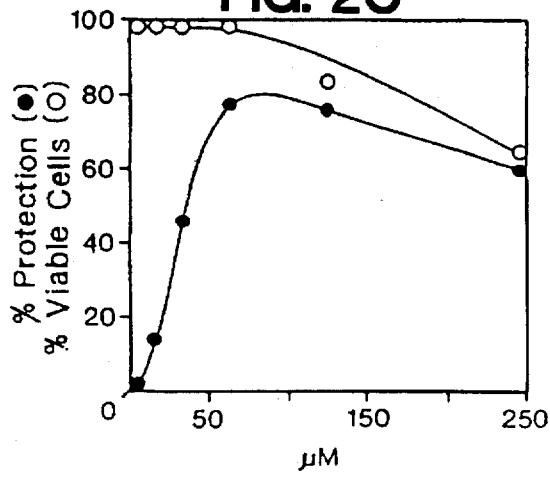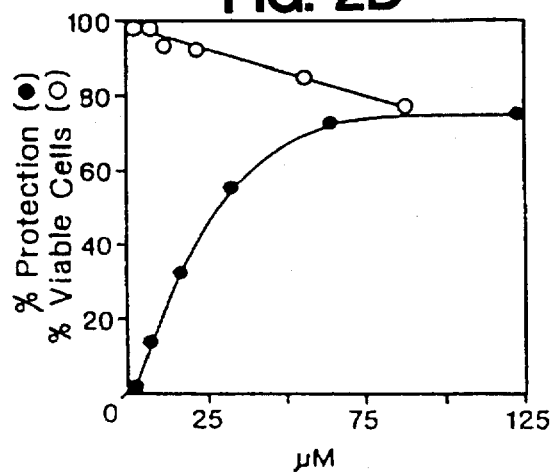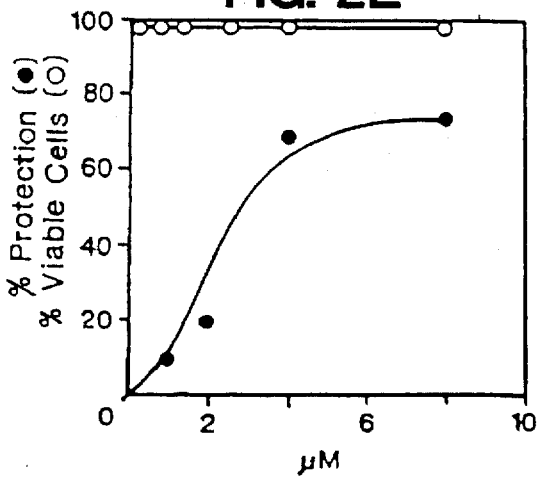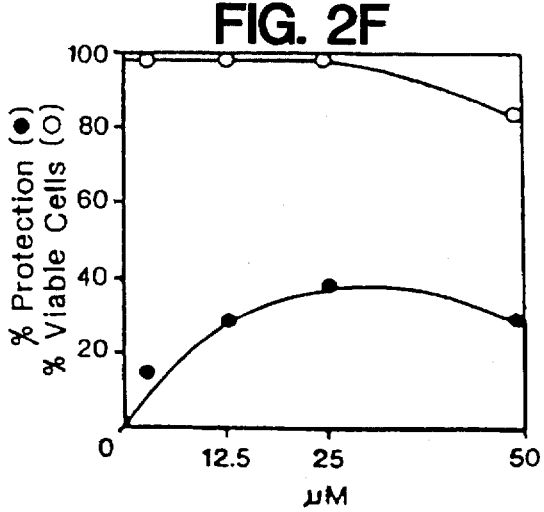

3'-DEOXY OR 3'-O-SUBSTITUTED-2',5'-OLIGOADENYLATES AS ANTIVIRAL AGENTS

CROSS-REFERENCE TO RELATED APPLICATIONS

This is a continuation of application Ser. No. 07/964,111, filed on Oct. 20, 1992, now abandoned, which is a continuation of application Ser. No. 07/613,848, filed as PCT/US89/02284, May 24, 1989, now abandoned, which is a continuation-in-part of application Ser. No. 204,659 filed Jun. 9, 1988, now abandoned, which is a continuation-in-part of application Ser. No. 144,602, filed Jan. 11, 1988, now U.S. Pat. No. 4,859,768, which is a continuation of application Ser. No. 629,660, filed Jul. 11, 1984, now abandoned. The disclosure of application Ser. No. 204,659 is incorporated herein by reference.

REFERENCE TO GOVERNMENT GRANT

The invention described herein was supported by National Institutes of Health Grant GM-26134 and National Science Foundation Grant PCM-8111752.

FIELD OF THE INVENTION

The invention relates to certain therapeutic uses of 2',5'-oligoadenylate analogs and pharmaceutical compositions of such analogs.

BACKGROUND OF THE INVENTION

The full nomenclature of the subject matter of the present invention involves extremely long terms. It is customary for those skilled in the art to abbreviate these terms in a manner well known to them. These general and customary abbreviations are set forth herein below and may be utilized in the text of this specification.

Abbreviations

A, adenosine or adenylate or adenylyl cordycepin or C or 3'-dA, 3'-deoxyadenosine(3'-deoxyadenylate)

ara-A, 9-β-D-arabinofuranosyladenine

EHNA, erthyro-9-(2-hydroxy-3-nonyl)adenine

A-3'-amino, 3'-amino-3'-deoxyadenosine tubercidin, 4-amino-7-(β-D-ribofuranosyl)pyrrolo-[2,3-d]pyrimidine 3'-dATP, 3'-deoxyadenosine triphosphate ATP, adenosine triphosphate I, inosine or inosinate or inosinylyl Xylo-A or xyloadenosine, 9-β-D-xylofuranosyladenine dCF or 2'-deoxycoformycin, (R)-3-(2-deoxy-β-D-erythropentofuranosyl)-3,6,7,8-tetrahydroimidazo[4,5-d][1,3]diazepine-8-ol 2–5A or 2',5'-oligo(A) or 2',5'-oligoadenylate, oligomer of adenylic acid with 2',5'-phosphodiester linkages and a triphosphate at the 5'-end 2',5'-cordycepin analog or 2',5'-oligocordycepin, oligomer of 3'-deoxyadenylic acid with 2',5'-phosphodiester linkages and a triphosphate at the 5'-end 2',5'-$A_n$ or core oligomer, oligomer of adenylic acid with 2',5'-phosphodiester linkages 2',5'-$A_3$ or 2',5'-adenylate trimer core, adenylyl-(2',5')adenylyl(2',5')adenosine 2',5'-$A_4$ or 2',5'-adenylate tetramer core, adenylyl(2',5')adenylyl(2',5')adenylyl(2',5')adenosine 2',5'-3'$dA_3$ or 2',5'-C-C-C or 2',5'-cordycepin trimer core, 3'-deoxyadenylyl(2',5')3'-deoxyadenylyl-(2',5')3'-deoxyadenosine 2',5'-C-C-C-C or 2',5'-cordycepin tetramer core, 3'-deoxyadenylyl (2',5')3'-deoxyadenylyl(2',5')3'-deoxyadenylyl(2',5')3'-deoxyadenosine 3',5'-$A_3$, adenylyl (3',5')adenylyl(3',5')adenosine 2',5'-$I_3$ or 2',5'-inosine trimer core, inosinylyl-(2',5')inosinylyl(2',5')inosine EBV, Epstein-Barr virus EBNA, Epstein-Barr virus associated early nuclear antigen HIV, human immunodeficiency virus, including HIV-1, HIV-2, and all other HIV subtypes HBLV, human B-cell lymphotropic virus HTLV, human T-cell leukemia virus, including HTLV-I, HTLV-II and HTLV-III, and all other HTLV sub-types IFNα: α-interferon rIFN-αA: recombinant α-interferon dsRNA: double-strand ribonucleic acid 2',5'-A-A-Tu, adenylyl(2',5')adenylyl(2',5')tubercidin 2',5'-Tu-Tu-Tu, 2',5'-tubercidylyl(2',5') tubercidylyl(2',5') tubercidin 2',5'-A-A-ara-A, adenylyl (2',5')adenylyl(2',5') ara-A 2',5'-C-C-A, 3'-deoxyadenylyl(2',5')3'-deoxyadenylyl(2',5')adenosine 2',5'-A-C-C, adenylyl(2',5')3'-deoxyadenylyl-(2',5')3'-deoxyadenosine 2',5'-A-A-C, adenylyl(2',5')adenylyl(2',5')3'-deoxyadenosine 2',5'-C-A-C, 3'-deoxyadenylyl(2',5')adenylyl-(2',5')3'-deoxyadenosine 2',5'-C-C-A, 3'-deoxyadenylyl(2',5')3'-deoxyadenylyl(2',5') adenosine 2',5'-A-C-A, adenylyl(2',5')3'-deoxyadenylyl-(2',5') adenosine 2',5'-xylo-$A_3$, xyloadenylyl(2',5')xyloadenylyl-(2',5') xyloadenosine 2',5'-xylo-$A_4$, xyloadenylyl(2',5')xyloadenylyl-(2',5') xyloadenylyl(2',5')xyloadenosine Ac, acetyl Bz, benzyl MMTr, 5'-O-p-methoxytrityl 2',5'-trityl-$C_3$, 5'-O-p-methoxytrityl-3'-deoxyadenylyl(2',5')3'-deoxyadenylyl(2',5')3'-deoxyadenosine 2',5'-trityl-$A_3$, 5'-O-p-methoxytrityladenylyl-(2',5') adenylyl(2',5')adenosine 2',5'-C-C-dCF, 3'-deoxyadenylyl(2',5')3'-deoxyadenylyl (2',5')2'-deoxycoformycin 2',5'-A-A-A-3'-amino, adenylyl(2',5')adenylyl-(2',5')3'-amino-3'-deoxyadenosine SiTBD, t-butyldimethylsilyl or —Si(CH$_3$)$_2$C(CH$_3$)$_3$ 2',5'-$A_{(Si)}$-$A_{(Si)}$-A, 3'-O-t-butyldimethylsilyladenylyl(2',5')3'-O-t-butyldimethylsilyladenylyl(2',5')adenosine 2',5'-A-A-A-3'-O-methyl, adenylyl(2',5')adenylyl-(2',5') 3'-O-methyladenosine 2',5'-A-A-A-3'-O-pentyl, adenylyl(2',5')adenylyl-(2',5')3'-O-pentyladenosine 2',5'-A-A-A-3'-O-hexyl, adenylyl(2',5')adenylyl-(2',5')3'-O-hexyladenosine 2',5'-A-A-A-3'-O-heptyl, adenylyl(2',5')adenylyl-(2',5')3'-O-heptyladenosine 2',5'-EHNA-A-A, erythro-9-(2-hydroxy-3-nonyl)adenylyl(2',5')adenylyl(2',5')adenosine The abbreviation for the "tetramer" compounds comprising the adenylyl (A) and 3'deoxyadenylyl (C) moieties is illustrated by the following:

2',5'-A-A-C-C, adenylyl(2',5')adenylyl(2',5')3'-deoxyadenylyl(2',5')3'-deoxyadenosine With the expansion of the knowledge of the antiviral state induced by interferon, attention has been focused on the chemical and enzymatic synthesis and biological properties of the 2',5'-oligoadenylates as mediators of the antiviral response. 2',5'-Oligo(A) is a component of a natural, broad-spectrum antiviral defense mechanism in plants and animals. The 2-5A pathway, also known as the 2-5A/RNase L pathway or antiviral system, is widely accepted to be involved in the antiviral mechanism of interferon, and may also be involved in the regulation of cell growth and differentiation. According to that pathway, 2-5A is synthesized from ATP by 2',5'-oligoadenylate synthetase [ATP: (2'-5')oligo(A)-adenyltransferase (EC 2.7.7.19)], hereinafter "2-5A synthetase". The enzyme is activated by dsRNA. 2-5A exerts its biological effects by binding to and activating its only known target enzyme, the unique 2-5A dependent endoribonuclease RNase L. The latter cleaves viral and cellular mRNA or rRNA, thereby inhibiting protein synthesis. Hovanessian et al., *Eur. J. Biochem.* 93:515–526 (1979); Kerr et al., *Proc. Natl. Acad. Sci. USA* 75:256–260 (1978). However, the short half-life of the authentic 2-5A molecule in biological systems is an acknowledged disadvantage in the control of viral replication.

"Human B-lymphotropic virus", also known as "human B-cell lymphotropic virus" (HBLV), which is characterized by a large molecular weight double-stranded DNA genome is morphologically similar to viruses of the herpes virus family, but is readily distinguishable from the known human and non-human primate herpes viruses by host range, in vitro biological effects, antigenic features and genome. Salahuddin et al., *Science* 234:596–601 (1986); Josephs et al., *Science* 234:601–602 (1986). The virus has been observed to selectively infect freshly isolated human B-cells, which are converted into large, refractile mono- or binucleated cells with nuclear and cytoplasmic inclusion bodies. HBLV is suspected to be the cause of a chronic mononucleosis-like syndrome characterized by chronic fatigue lasting more than a year.

Human immunodeficiency virus ("HIV"), also known as human, T-cell leukemia virus III ("HTLV-III"), the etiologic agent of acquired immune deficiency syndrome, is a type D retrovirus. As in all retroviruses, an essential feature of HIV replication is reverse transcription of the plus-strand RNA genome into DNA, a process which requires an RNA dependent DNA polymerase, reverse transcriptase. This enzyme is viral-encoded and is found associated with genomic RNA in mature HIV virions. The exclusiveness of reverse transcriptase to retroviruses and viruses requiring a short reverse transcription step makes reverse transcriptase a major target for antiviral, and particularly for antiretroviral, therapeutic intervention.

What is needed is a method for controlling HIV, chronic fatigue caused by HBLV, and other disease states characterized by a 2-5A pathway defect using compounds that are more metabolically stable and active than authentic 2-5A.

SUMMARY OF THE INVENTION

In accordance with the invention, a method of treating a mammal for a disorder characterized by a 2-5A pathway defect is provided. The method comprises administering to such mammal at least one compound of the formula:

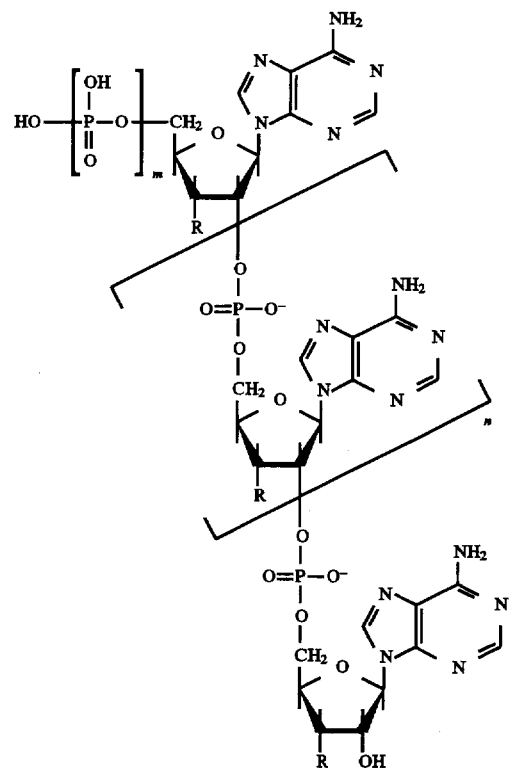

wherein n is a whole positive integer from 1 to 8 m is 0, 1, 2, or 3, and each R, same or different, is selected from hydrogen, hydroxy, amino, $C_1$–$C_{10}$-alkoxy and —$OSi(CH_3)_2C(CH_3)_3$, provided that all R groups may not be hydroxy in the same compound, or a pharmaceutically acceptable salt thereof.

Preferably, n is from 1 to 3, more preferably 1 or 2. Most preferably, the R group on the 2'-terminal nucleotide is other than hydroxy, that is, the 2'-terminal nucleotide is other than adenosine.

Examples of compounds for use in the method of the invention include the following core compounds, their corresponding 5' mono-, di-, and triphosphates, and the pharmaceutically acceptable salts of any of them:

Compounds Wherein R is Selected from Hydrogen and Hydroxy

2',5'-C-C-C,

2',5'-A-A-C,

2',5'-A-C-C,

2',5'-C-C-A,

2',5'-C-A-C,

2',5'-C-C-A, and

2',5'-A-C-A, in addition to the various "tetramer" combinations of A and C, including but not limited to,

2',5'-C-C-C-C,

2',5'-A-A-A-C,

2',5'-A-A-C-C,

2',5'-A-A-C-A, and the like.

Compounds Wherein R is Selected from Hydroxy and $C_1$–$C_{10}$ Alkoxy, in Particular $C_1$–$C_7$ Alkoxy, Such As 2',5'-A-A-A-3'-O-methyl 2',5'-A-A-A-3'-O-pentyl 2',5'-A-A-A-3'-O-hexyl 2',5'-A-A-A-3'-O-heptyl Compounds Wherein R is Selected from Hydroxy and Amino, Such As 2',5'-A-A-A-3'-amino Compounds Wherein R is Selected from Hydroxy and $OSi(CH_3)_2C(CH_3)_3$, Such As 2',5'-$A_{(Si)}A_{(Si)}$A In a related invention, a method of treating a mammal for a disorder characterized by a 2–5A pathway defect comprises administering to such mammal at least one compound selected from the group of 2',5'-A-A-ara-A, 2',5'-A-A-Tu, 2',5'-Tu-Tu-Tu,

2',5'-$I_3$,

2',5'-xylo-$A_3$,

2',5'-xylo-$A_4$,

2',5'-C-C-dCF,

2',5-EHNA-A-A, and 5,6-dichlorobenzimidazylyl(2',5')5,6-dichlorobenzimidazylyl(2',5')5,6-dichlorobenzimidazole riboside, or the 5' mono-, di- and triphosphate thereof, or a pharmaceutically acceptable salt of any of them.

The invention is further directed to pharmaceutical compositions for the treatment of a mammal for any disorder characterized by a 2–5A pathway defect, comprising at least one of the herein described compounds and a pharmaceutically acceptable carrier.

BRIEF DESCRIPTION OF THE FIGURE

FIGS. 2A through 2F show the effect of the following on HIV-1 infection in vitro: (2A) cordycepin, (2B) 2',5'-$A_3$, (2C) 2',5'-$C_3$ and (2D) 2',5'-$pC_3$, (2E) (2',5')-A-C-A and (2F) 2',5'-$pC_4$. MT-2 cells were challenged with HTLV-III$_B$ in the presence and absence of effectors. Cytopathic effect was quantitated by vital dye uptake as described in Example 9. Each data point represents the average of three values. Standard deviations were less than 10% of averaged values.

DETAILED DESCRIPTION OF THE INVENTION

Figure 1:
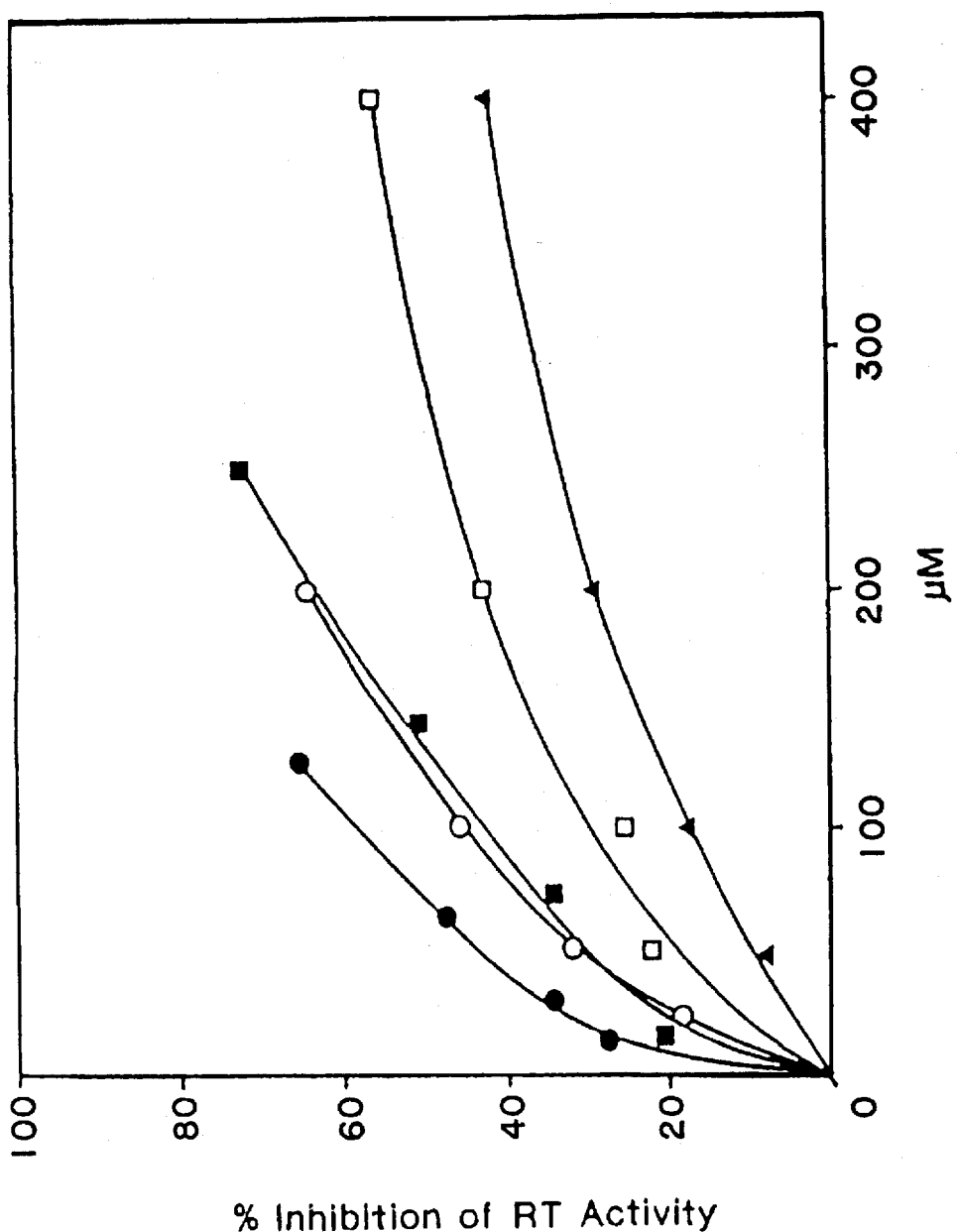
FIG. 1 shows the effect of HIV-1 reverse transcriptase inhibition by the following 2',5'-oligoadenylate analogs: $p_2C_3$ (solid circles); $pC_4$ (hollow circles); $p_3C_3$ (solid squares); $pC_3$ (hollow squares); $C_3$ (solid triangles). Reverse transcriptase reactions contained poly(A)-(dT)$_{15}$ as template-primer, Triton X-100 activated HTLV-III$_B$ lysates as enzyme, and were monitored by [$^3$H]dTTP incorporation as described in Example 9. Control values averaged 129,000 cpm, while background values averaged 10,000 cpm.

Administration of exogenous, metabolically stable analogs of 2–5A will render increased protection against disorders characterized by a 2–5A defect, particularly protection against retroviral infection in animals and humans. By "2–5A defect" as used herein is meant any manifestation, condition or interruption of the 2–5A pathway which results in a decrease in the production of authentic 2–5A, and/or the interruption of 2–5A-dependent activation of RNase L. Afflictions characterized by a 2–5A defect include, for example, the following: retroviral infection, particularly HTLV infection, most particularly HIV infection, chronic fatigue, and cutaneous T-cell lymphoma; chronic myelogenous leukemia; acute leukemia; cancer; T-cell leukemia; Alzheimer's disease; Parkinson's disease; multiple sclerosis; autoimmune disease; and surgery- and other trauma-induced immune dysfunction.

The defect is apparent in diseases, such as the above disorders caused by chronic viral infection, immune cell defects or both. 2–5A pathway defects are particularly manifested in diseases characterized by both chronic viral infection and immune cell defects.

Structural modification of the 2–5A molecule at the 3'-hydroxyl groups and elsewhere provides 2–5A analogues with remarkably increased metabolic stability to 2'-phosphodiesterases and cellular nucleuses, while maintaining the ability to activate RNase L. Likewise modification of native 2–5A by substitution of the terminal nucleotide results in a more stable molecule. Persistent, high intracellular concentration of the metabolically stable 2–5A analogs are a consequence of their increased stability.

The longer-lasting pharmacological activity of the 2–5A analogs offer a more favorable therapeutic ratio. This allows a decreased frequency of administration relative to 2–5A, which is metabolicly unstable. Decreased frequency of administration is important due to the chronic nature of many afflictions characterized by 2–5A pathway defects.

The 2–5A analogs are particularly useful in the treatment of infections caused by retroviruses. The 2–5A pathway defect associated with retroviral infection comprises the inactivation of the pathway caused by the virus' interference with the activation of 2–5A synthetase by dsRNA. In the absence of 2–5A synthetase activation, 2–5A production, and hence activation of RNase L, is reduced. According to the present invention, exogenous, metabolically stable 2–5A analog is administered to counteract this retrovirally-caused defect in the 2–5A pathway. The 2–5A analogs, like authentic 2–5A, are capable of activating RNase L, which cleaves viral RNA.

The 2–5A analogs are particularly useful in protecting against infection by the various human T-cell leukemia viruses (collectively "HTLV"), such as HTLV-I, which cause cutaneous T-cell lymphoma; HTLV-II, which causes Sezany lymphoma: HTLV-III; and HTLV-IV, which is presently believed to be the etiologic agent of multiple sclerosis. Each of the HTLV viruses is a retrovirus. Also known as "HIV-1", HTLV-III is responsible for causing acquired immune deficiency syndrome ("AIDS"). The compounds are further believed useful in treating HIV-2, a second serologically distinct HIV subtype. Hereinafter (HIV) shall mean either HIV-1 or HIV-2, and any other HIV subtypes now or hereinafter known.

HTLV-infected patients, in particular HIV-1-infected patients, have been shown to demonstrate unusually low levels of 2–5A and/or RNase L activity in blood mononuclear cells. Blood mononuclear cells from healthy individuals, by contrast, display higher 2–5A levels, on average, and RNase L activity is readily detectable. Likewise blood mononuclear cells of chronic fatigue-inflicted individuals exhibit low 2–5A levels, and evidence the appearance of novel RNA cleavage products, distinct from the specific cleavage products observed in blood mononuclear cells from normal individuals.

While the practice of the invention is illustrated herein with regard to the treatment of HIV-1 infection, which is generally regarded as a prototypical retrovirus, the method of the invention has application to the treatment of any diseases wherein the etiologic agent comprises a retrovirus. Additional retrovirus which infect man include, for example, the various non-HIV HTLV virus, discussed above.

The various afflictions characterized by a 2–5A pathway defect, in particular retroviral infection, most particularly HIV infection, may therefore be treated by the administration of exogenous, metabolically stable analogs of 2–5A to counteract the 2–5A system defect associated with the disease state.

For pharmaceutical use, the 2',5'-oligoadenylate analogs may be taken up in pharmaceutically acceptable carriers. Such carriers for preparation of pharmaceutical compositions of the invention may be either organic or inorganic, solid or liquid in nature. Suitable solid carriers include gelatin, microcrystalline cellulose, lactose, starches, and magnesium stearate. Suitable liquid carriers include water and alcohols such as ethanol, benzyl alcohol and poly (ethylene glycols). The preferred liquid carriers for injectable preparations include water, saline solution, dextrose solution and glycol solutions such as aqueous propylene glycol or aqueous poly(ethylene glycol). The properties of the formulations may be enhanced by the addition of one or more adjuvants possessing properties as viscosity enhancers, surfactants, pH modifiers, preservatives, sweeteners, stability enhancers, coloring agents, suspending agents, granulating agents, coating agents, disintegration modifiers, propellants, emulsifying agents and hymectants. The resulting compositions may be in the form of solutions, suspensions, tablets, capsules, ointments, elixirs, injectable compositions and the like.

The dosage administered depends upon the severity of the infection or affliction and the size and weight of the subject. The dosage may vary .over a wide range depending on the nature of the affliction, and the size and weight of the subject. According to one embodiment, the compounds are prepared as a solution of 0.1–100 mg/ml in water, phosphate buffered saline or other appropriate fluid, or may be prepared as a tablet containing 0.01–1 gram active compound.

The compounds may be administered in the form of water-soluble salts. Pharmaceutically acceptable water-soluble salts include, for example, the sodium, potassium and ammonium salts of the active compounds. They are readily dissolved in water or saline solution. The formulation may contain additional agents, such as a sugar or protein, to maintain the osmotic balance.

The 2',5'-oligoadenylate analogs may be administered in doses of about 0.1 mg to about 1 gram to animals or humans afflicted by, or suspected of affliction by, or at risk of affliction by, any of the various conditions characterized by a 2–5A pathway defect. The total daily dosage may vary, for example, from about 0.001 gram to about 1 gram, although lower or higher amounts may be administered. A preferred daily dose is from about 0.01 gram to about 0.1 g of active ingredient. The compounds may be administered by any of several routes, including, but not limited to, intravenous injection, intraperitoneal or intramuscular injection, and oral administration. Techniques for accomplishing such administration are routine and known in the medical art. Administration may be as frequent as several times a day or as infrequent as weekly. For intravenous injection, particularly for treatment of HIV, a solution containing about 0.1 to about 1.0 milligram per ml of active ingredient is preferred.

It is also contemplated that the 2',5'-oligoadenylate analogs may be administered topically to treat skin lesions associated with any of the disease states characterized 2–5A pathway defect. A sufficient amount of a preparation containing one or more of the 2',5'-oligoadenylate analogs may be applied to cover the lesion or affected area. An effective concentration of active agent is from about $10^{-3}$M to about $10^{-5}$M, with about $10^{-4}$M being preferred.

In addition to administration with conventional carriers, the 2–5A analogs may be administered by a variety of specialized oligonucleotide or nucleic acid delivery techniques, such as by encapsulation in unilameller liposomes or reconstituted sendai virus envelopes, or by conjugation to carrier molecules such as poly(L-lysine). Such methods are disclosed in commonly-assigned co-pending U.S. Pat. No. 4,924,624, corresponding to International Patent Application WO 89/03683, the entire disclosure of which is incorporated herein by reference.

The 2',5'-oligoadenylate analogs may be chemically synthesized as follows. A blocked adenosine-2'-phosphodiester is prepared by blocking the 6-amino position with benzoyl, blocking the 5' position with p-methoxytrityl and optionally blocking the 3' position with t-butyldimethylsilyl. A blocked nucleoside is prepared by blocking the 2' and 3' positions with acetyl, benzoyl or t-butyldimethylsilyl. Preparation of suitably blocked adenosine-2'-phosphodiesters is carried out by adding the t-butyldimethylsilyl group to the 3'-O-t-butyldimethylsilyl-isomeric-3'-hydroxyl group of $N^6$-benzoyl-5'-O-(4-methoxytrityl)adenosine by condensing the latter compound with t-butyldimethylsilylchloride using imidazole in pyridine to yield the 3'-O-t-butyldimethylsilyl derivative. Phosphorylation of the derivative is carried out using 2,5-dichlorophenyl-phosphorotriazolide in pyridine to yield a suitably blocked adenosine-2'-phosphodiester. This preparation is described in R. Charubala, E. Uhlmann, and W. Pfleiderer, Liebigs Ann. Chem., 2392 (1981) and R. Charubala, W. Pfleiderer, Tetrahedron Lett. 21, 4077 (1980), which are specifically incorporated herein by reference. The blocked adenosine-2'-phosphodiester is condensed with the blocked nucleoside in the presence of a condensing reagent which causes blocking of the phosphate functions to form a fully protected dinucleosidemonophosphotriester.

The resulting fully protected condensate is then detritylated at the terminal 5' position with a detritylating agent and condensed with a further adenosine-2'-phosphodiester, blocked as described above, to form a fully protected 2',5'-trinucleosidediphosphoditriester, or 2',5' trimer core The fully protected trimer core is then treated with appropriate deprotecting reagents to achieve complete deprotection and conversion to 2',5' trimer core.

Alternatively, those 2',5-oligoadenylate analogs which are formed from nucleotides which are substrates for 2–5A synthetase may be prepared enzymatically, according to the procedure of U.S. Pat. No. 4,464,359, the entire disclosure of which is incorporated by reference.

Preparation of the trimer core 2',5'-A-A-ara-A is reported in Engles, J., Tetrahedron Lett. 21, 4339 (1980), which is specifically incorporated herein by reference. Accordingly, the nucleoside $N^6$, 2'-O-,3'-O-tribenzoylarabinofuranosyladenine is condensed with the fully protected $N^6$, 3'-O-dibenzoyl-5'-O-trityladenylyl(2'-O-tribromoethyl-5')$N^6$ 3'-O-dibenzoyladenosine-2'-

(tribromoethylcyanoethylphosphate) using as the coupling reagent quinoline-8-sulfonyl-3-nitro-1,2,4-triazolide. The final deprotection of the resulting trimer triester is performed by detritylation with boron trifluoride/methanol followed by electrochemical deblocking ($CH_3CN$, Hg pool, $NaHCO_3$ in the anolyte) of the tribromoethyl moiety. The debenzoylation of the diester is accomplished using butylamine/methanol to form adenylyl-(2',5')adenylyl(2'-5')9-β-D-arabinofuranosyladenine.

Preparation of 2',5'-$I_3$ is described in Charubala et al., Tetrahedran Lett. 23, 4789 (1982), which is specifically incorporated herein by reference.

Preparation of the trimer core 2',5'-Xylo-$A_3$ and tetramer core 2',5'-xylo-$A_4$ is reported in Grosselin, G. and Imbach, J. L., Tetrahedron Lett. 22, 4699 (1981), which is incorporated herein by reference. Accordingly, the trimer and tetramer core Xylo-$A_3$ and Xylo-$A_4$ are synthesized by treating $N_6$-3'-O-dibenzoylated xylofuranose with t-butyldimethylsilyl-chloride to yield the silylated derivative of $N_6$-3'-O-dibenzoylated xylofuranose which is debenzoylated with sodium methoxide to form the 2'-silyl derivative. The primary hydroxyl of the 2'-silyl derivative is protected with a monomethoxytrityl group and the resulting 5'-tritylated-2'-silyl derivative is reacted with an equimolar equivalent of benzoic anhydride dissolved in pyridine in the presence of 4-dimethylaminopyridine to yield the $N^6$ and 3-O-benzoylated-5'-tritylated-2'-silylated derivative. Removal of the t-butyldimethylsilyl group with tetrabutylammonium fluoride gives the $N^6$ and 3-O-dibenzoylated-5'-tritylated derivative which is successively benzoylated and detritylated to produce $N^6$, 2',3'-O-tribenzoylxyloadenosine.

The previous $N^6$ and 3-O-dibenzoylated-5'-tritylated derivative is also reacted with an excess of o-chlorophenyl-phosphoro-di-(1,2,4-triazolide) in an acetonitrile-pyridine mixture followed by a reaction with aqueous triethylamine to form the 2'-phosphotriester. The phosphotriester is condensed with $N^6$, 2',3'-O-tribenzoylxyloadenosine in the presence of 1-mesitylenesulfonyl-3-nitro-1,2,4-triazole to yield the fully protected dinucleosidephosphotriester which is detritylated by treatment with p-toluenesulfonic acid in a mixture of chloroform and methanol (4:3). A final condensation between the detritylated product and the phosphotriester and purification by silica gel chromatography yields the fully protected trinucleosidediphosphotriester (blocker trimer core). The fully deblocked trimer core is obtained by treatment of the blocked trimer core with tetramethylguanidinium-syn-4-nitrobenzaldoximate, aqueous ammonia, and 80% acetic acid.

EHNA is prepared according to Evans et al., *J. Am. Chem. Soc.*, 92:4751 (1970). It may thereafter be condensed with suitably blocked adenosine by following the protection, condensation and deprotection methods described herein to form 2',5'-EHNA-A-A. In the same manner, 2',5'-C-C-dCF is prepared from dCF and adenosine. Methods for the preparation of dCF are set forth in U.S. Pat. No. 3,923,785 and Baker et al., *J. Am. Chem. Soc.* 101:6127 (1979), both incorporated herein by reference. Likewise, the 2-5A analog 5,6-dichlorobenzimidazylyl-(2',5')5,6-dichlorobenzimidazylyl-(2',5')5,6-dichlorobenzimidazole riboside is prepared by condensing commercially available 5,6-dichlorobenzimidazole riboside (Sigma, Cat. No. D5893) according to similar methods.

The preparation of the 2',5'-oligoadenylate analogs utilized in the practice of the invention is illustrated in the following non-limiting examples.

EXAMPLE 1

Preparation of Structurally Modified 2',5'-Adenylate Trimer Cores

The various structurally modified novel trimer core analogs of 2',5'-adenylate may generally be prepared as follows.

One mmole of suitably blocked adenosine-2'-phosphodiester having the general formula of reactant (I) was prepared from adenosine or cordycepin according to the method of Charubala, R., Uhlmann, E., and Pfleiderer, W., Liebigs Ann. Chem., 2392 (1981) and Charubala, R., and Pfleiderer, W., Tetrahedron Lett. 21, 4077 (1980). Examples of suitably blocked adenosine-2'-phosphodiesters are represented by compounds 1 and 2, listed in Table 1.

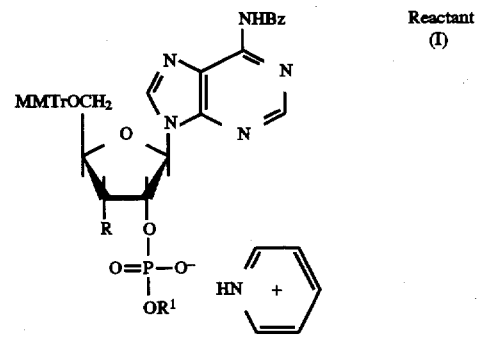

TABLE 1

| Compound Name | Compound No. | R | $R^1$ |
|---|---|---|---|
| Pyridinium $N^6$benzoyl-3'-O-t-butyldimethylsilyl-5'-O-p-methoxytrityladenosine-2-(2-chlorphenyl)-phosphate | 1 | OSiTBD | 2-chlorophenyl |
| Pyridium $N^6$-benzoyl-5'-o-p-methoxytrityl-3'-deoxyadenosine-2'-(2-chlorophenyl)-phosphate | 2 | H | 2-chlorophenyl |

Reactant (I) was combined with a blocked nucleoside having the general formula of reactant (II) below. Reactant (II) is exemplified by compounds 3–9 listed in Table 2.

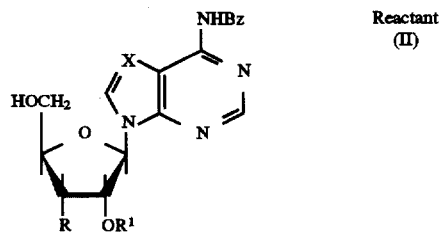

TABLE 2

| Compound Name | Compound No. | R | R¹ | X |
|---|---|---|---|---|
| $N^6$-benzoyl-2',3'-di-O-t-butyldimethylsilyl-adenosine | 3 | OSiTBD | SiTBD | N |
| $N^6$,2'-o-dibenzoyl-3'-deoxyadenosine | 4 | H | Bz | N |
| $N^6$-benzoyl-2'-O-acetyl-3'-deoxyadenosine | 5 | H | Ac | N |
| $N^6$,2'-O-dibenzoyl-3'-O-n-pentyladenosine | 6 | O-n-$C_5H_{11}$ | Bz | N |
| $N^6$,2'-O-dibenzoyl-3'-O-n-heptyladenosine | 7 | O-n-$C_7H_{15}$ | Bz | N |
| $N^6$-benzoyl-2'-O-t-butyldimethylsilyl-3'-p-nitrophenyl-ethoxycarbonylamino-3'-deoxyadenosine | 8 | 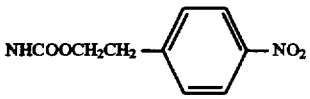 | SiTBD | N |
| 2',3'-di-O-t-butyl-dimethylsilyl-tubercidin | 9 | OSiTBD | SiTBD | CH |

Compounds 3 and 9 are prepared treating $N^6$-benzoylated adenosine with monomethoxytrityl chloride in pyridine to yield the 5'-monomethoxytrityl derivative. The derivative is treated with t-butyldimethylsilylchloride in a mixture of pyridine and methylimidazole to form the $N^6$-benzoyl-2',3'-di-O-t-butyldimethylsilyl-5'-monomethoxytrityladenosine. The trityl group is removed by acetic acid to produce compound 3. Compound 9 is synthesized analogously, starting with $N^6$-benzoylated tubercidin. This method of preparation is a described in Charubala, et al., Liebigs Ann. Chem. 2392 (1981).

Compound 4 is prepared by treating $N^6$-benzoylated-3'-deoxyadenosine with monomethoxytritylchloride to yield $N^6$-benzoyl-5'-O-monomethoxytrityl-3'-deoxyadenosine, which is converted to $N^6$-2'-O-dibenzoyl-3'-deoxyadenosine by benzoylation of the 2'-hydroxyl group with benzoylchloride followed by detritylation with 80% acetic acid for 30 minutes. This method of preparation is as described in Tetrahedron Lett. 21, 4077 (1980).

Compound 5 is prepared by converting $N^6$-benzoyladenosine with t-butyldiphenylchlorosilane to the 5'-silylated nucleoside in pyridine. The 5'-silylated nucleoside is treated with triethyl orthoacetate followed by boron trifluoride/diethyl ether and sodium iodide in $CH_3CN$ (0° C., 1 hour) to yield the 3'-iodoacetyl derivative. The iodoacetyl derivative is converted to compound 5 by treatment with tributyltinhydride in toluene (80° C., 1 hour) and desilylation with ammonium tetrabutyl fluoride in tetrahydrofuran. This method of preparation is as described by Eagles, J., in Tetrahedron Lett. 21, 4339 (1980), which is incorporated herein by reference.

Compounds 6 and 7 are prepared by treating $N^6$-benzoyl adenosine with tritylchloride in pyridine and refluxing for 2 hours. $N^6$-benzoyl-5'-trityladenosine is isolated by extraction with chloroform. The water from the chloroform phase is removed by drying with sodium sulfate $N^6$-benzoyl-2',5'-di-O-trityladenosine and $N^6$-benzoyl-3',5'-di-O-trityladenosine are isolated by preparative silica gel thin layer chromatography in chloroform/ethanol. Compounds 6 and 7 are prepared by treating the isolated compounds with n-pentylchloride and n-heptylchloride, respectively, under reflux in a suspension of sodium hydroxide in benzene. The solution is neutralized by refluxing in acetic acid followed by the addition of diethyl ether and water. The reaction products are extracted with chloroform followed by thin layer chromatography with chloroform:methanol (4:1) on silica gel plates. The trityl and benzoyl groups are removed by refluxing in acetic acid for one hour, cooling, extraction with diethyl ether, followed by concentration and cooling to yield crystalline compounds 6 and 7. This method of preparation is carried out according to Blank, H. U., Franne, D., Myles, A. and Pfleiderer, W., Justus Liebigs Ann. Chem. 742, 34 (1970), which is incorporated herein by reference.

Compound 8 was prepared as follows. 1 mmole of 3'-amino-3'-deoxyadenosine was reacted with 1.2 mmole of 1-methyl-3-nitrophenylethoxy carboxylimidazolium chloride in dimethylformamide, followed by the addition of hexamethyldisilazane to block the 2',5' and 6-amino positions. 1.1 mmole of benzoyl chloride in pyridine was added at room temperature to produce blocked $N^6$-benzoyl-2',5'-disilyladenosine. The reaction mixture was poured into methanol-$NH_3$ to remove the 2' and 5' silyl groups. Reaction with MMTr chloride in pyridine yielded the 5'-MMTr derivative. Tert-butyldimethylsilyl chloride in a mixture of pyridine and 1-methylimidazole was then added to the 5'-MMTr derivative and 5'-detritylated as in Example 1 to form compound 8.

Reactants (I) and (II) were combined to produce the intermediate having the general formula of dimer (III) as follows. 0.95 Mmole of reactant (II) and condensing reagents 2,4,6-triisopropylbenzenesulfonyl chloride (2 mmole) and 1-methylimidazole (6 mmole) were combined and stirred for 1 hr at room temperature. The reaction is stopped by adding 30 ml of aqueous phosphate buffer pH 7 and extracted with 150 ml of chloroform. The chloroform layer was washed twice with 50 ml of water, dried over sodium sulfate about 1–2 hrs and filtered. The chloroform was evaporated to a small volume and then applied to a silica gel column (20×2.5 cm) for purification. Chromatography was performed first with chloroform and then with chloroform/methanol (99/1, v/v) to elute the fully protected dinucleosidemonophosphotriester produce of the general formula of dimer (III). Evaporation gave a solid foam of dimer (III) exemplified by compounds 10–17 (Table 3).

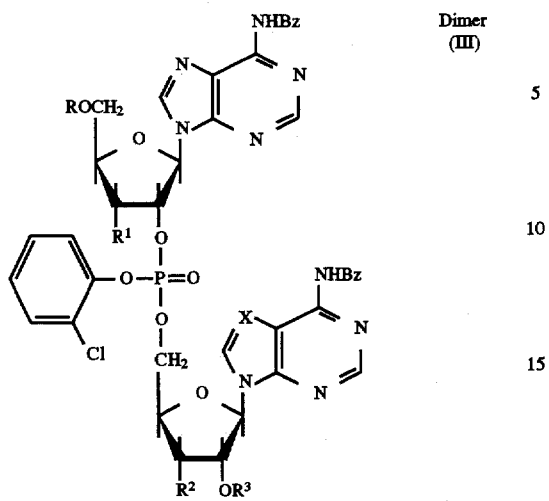

Dimer (III)

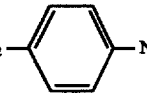

TABLE 3

| Compound No. | R | R¹ | R² | R³ | X | Compound No. | R |
|---|---|---|---|---|---|---|---|
| 10 | MMTr | OSiTBD | OBz | Bz | N | 18 | H |
| 11 | MMTr | OSiTBD | H | Ac | N | 19 | H |
| 12 | MMTr | OSiTBD | OSiTBD | SiTBD | CH | 20 | H |
| 13 | MMTr | OSiTBD | O-n-C$_5$H$_{11}$ | Bz | N | 21 | H |
| 14 | MMTr | OSiTBD | O-n-C$_7$H$_{15}$ | Bz | N | 22 | H |
| 15 | MMTr | H | OBz | Bz | N | 23 | H |
| 16 | MMTr | H | H | Bz | N | 24 | H |
| 17 | MMTr | OSiTBD | NHCOOCH$_2$CH$_2$—C$_6$H$_4$—NO$_2$ | SiTBD | N | 25 | H |

One mmole of the fully protected dimer (III) was stirred at room temperature for 30 minutes in 20 ml of 2% p-toluenesulfonic acid in dichloromethane/methanol (4/1, v/v) for detritylation. 20 ml of phosphate buffer pH7 was added and subsequently extracted several times with 200 ml of dichloromethane. The organic phase was washed with water, dried over sodium sulfate, evaporated to a small volume and then applied to a silica gel column (20×2.5 cm) for purification. Elution was performed with chloroform (400 ml) followed by chloroform/methanol (98/2, v/v/). Evaporation of the main fraction gave a 80–90% yield of the detritylated dinucleosidemonophosphotriester (dimer (III)), exemplified by compounds 18–25, (Table 3).

The fully protected 2',5'-trinucleosidediphosphoditriester, having the general formula of trimer (IV) and exemplified by compounds 26–34 (Table 4, below), was prepared from the 5'-detritylated dimer (III) as follows.

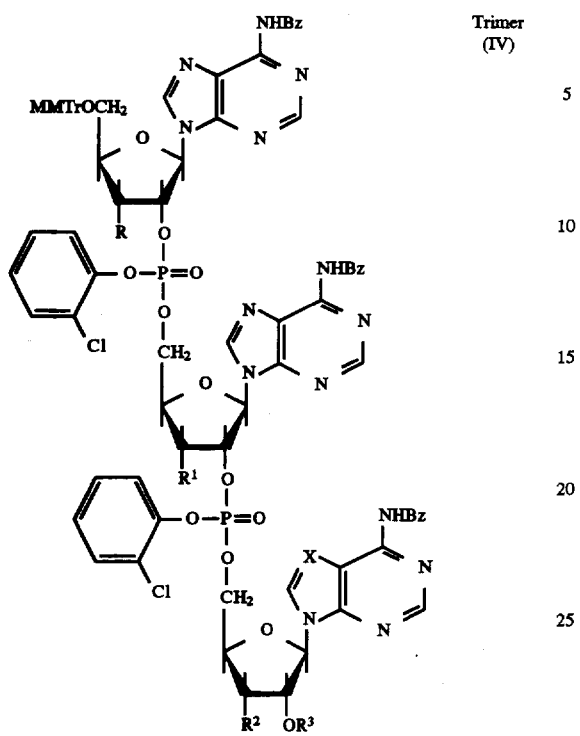

Trimer
(IV)

TABLE 4

| Compound No | R | R¹ | R² | R³ | X |
|---|---|---|---|---|---|
| 26 | H | OSiTBD | OBz | Bz | N |
| 27 | H | OSiTBD | H | Ac | N |
| 28 | OSiTBD | OSiTBD | OSiTBD | SiTBD | CH |
| 29 | OSiTBD | OSiTBD | O-n-C$_5$H$_{11}$ | Bz | N |
| 30 | QSiTBD | OSiTBD | O-n-C$_7$H$_5$ | Bz | N |
| 31 | OSiTBD | OSiTBD | OBz | Bz | N |
| 32 | H | H | OBz | Bz | N |
| 33 | OSiTBD | H | H | Bz | N |
| 34 | OSiTBD | OSiTBD | NHCOOCH$_2$CH$_2$—⟨C$_6$H$_4$⟩—NO$_2$ | SiTBD | N |

1.05 Mmole of the starting adenosine-2'-phosphodiester (reactant (I)), was condensed with 1 mmole of the 5'-detritylated dimmer (III) (compounds 18–25) in 10 ml of absolute pyridine using 3 mmole of 2,4,6-triisopropylbenzenesulfonyl chloride and 9 mmole of 1-methylimidazole as condensing agents. Work-up was performed after 2 hrs in the manner as described above. Quenching with phosphate buffer, followed by extraction with dichloromethane and silica gel chromatography in chloroform and chloroform/methanol (99/1/to 98/2, v/v) yielded 70–90% of fully protected trimer (IV) (compounds 26–34), as a chromatographically pure amorphous powder.

The fully protected 2'-5'-trinucleosidediphosphoditriester, trimer (IV), was deprotected to trimer core (V) as follows.

0.01 Mmole of trimer (IV) was treated with a solution of 0.073 g p-nitrobenzaldoxime and 0.07 g tetramethylguanidine in 2 ml of dioxane water (1/1, v/v) for 16 hrs at room temperature to deblock the o-chlorophenyl group. After evaporation to dryness and coevaporation four times with water, 20 ml of concentrated ammonium hydroxide was added and the solution stirred for 2 days at room temperature to deprotect the acyl groups. The solution was then evaporated again, and the residue was dissolved in 25 ml of water and washed four times with 10 ml of chloroform each time. The water layer was evaporated to dryness and coevaporated ten times with 10 ml absolute pyridine each time. The residue was then treated with 2 ml of an 0.5M solution of anhydrous tetrabutylammonium fluoride in absolute pyridine for 16 hrs to remove the t-butyldimethylsilyl groups. After evaporation, treatment of the residue with 5 ml of 80% acetic acid for 6 hrs at room temperature lead to cleavage of the p-methoxytrityl group. The solution was again evaporated, the residue dissolved in 15 ml of water, and extracted four times with 5 ml of chloroform each time. The aqueous layer was evaporated and then coevaporated several times with water until the smell of acetic acid disappeared. The residue was dissolved in 10 ml of water and applied to a DEAE-Sephadex A-25 column (60×1 cm) for ionexchange chromatography with a gradient of 0.001–0.5M triethylammonium bicarbonate. The main fraction was evaporated, then coevaporated several times with water. Trimer core (V), a fully deprotected 2',5'-trinucleosidediphosphate, was isolated by lyophilization of the aqueous solution to give 70–90% of an amorphous solid. Trimer core (V) is exemplified by compounds 34–45 (Table 5).

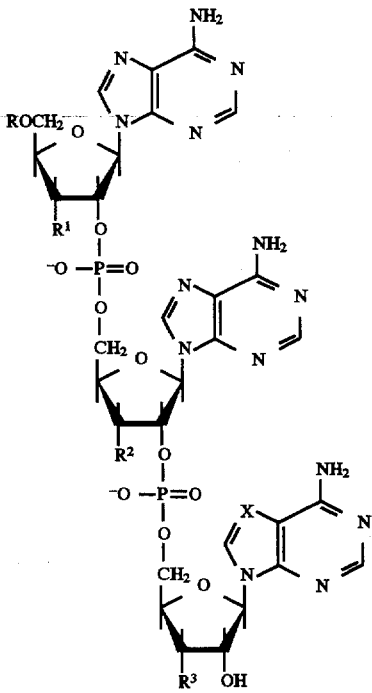

Trimer core (V)

treatment with tetrabutylammonium fluoride was omitted, in order to produce 2',5'-A$_{(Si)}$-A$_{(Si)}$-A (compound 40, Table 5).

EXAMPLE 3

Preparation of Adenylyl(2',5')adenylyl(2',5')3'-amino-3'-deoxyadenosine 0.01 Mmole of N$^6$-benzoyl-3'-O-t-butyldimethylsilyl-5'-O-p-methoxytrityladenylyl(2'-o-chlorophenyl-5')N$^6$-benzoyl-3'-O-t-butyldimethylsilyladenylyl(2'-o-chlorophenyl-5')N$^6$-benzoyl-2'-O-t-butyldimethylsilyl-3'-p-nitrophenylethoxycarbonylamino-3'-deoxyadenosine (compound 34, Table 4) was treated according to the deprotection procedure of Example 1 wherein the p-nitrophenylethoxycarbonyl group was cleaved simultaneously with the silyl groups by tetrabutylammonium fluoride in a β-elimination process. Subsequent decarboxylation yields 2',5'-A-A-3'-amino (compound 43, Table 5)

EXAMPLE 4

Preparation of 5'O-p-methoxytrityladenylyl(2',5') adenylyl(2',5')adenosine 0.01 Mmole of N$^6$-benzoyl-3'-O-t-butyldimethylsilyl-5'-O-p-methoxytrityladenylyl(2'-o-chlorophenyl-5')N$^6$-benzoyl-3'-O-t-butyldimethylsilyladenylyl(2'-o-chlorophenyl-5')N$^6$,N$^6$-2'-O,3'-O-tetrabenzoyladenosine prepared according to the method of Charubala, R., Uhlmann, E., and Pfleiderer, W., Liebigs Ann. Chem., 2392 (1981) was treated according to the deprotection procedure of Example 1 except that the last step of acetic acid treatment was omitted. The product, 2',5'-trityl-A$_3$ (compound 44, Table 5) was isolated, purified by DEAE-Sephadex A-25 chromatography, and lyophilized to form the amorphous pure compound 44 as a powder in 85% yield.

TABLE 5

| Compound Name | Compound No. | R | R$^1$ | R$^2$ | R$^3$ | X |
|---|---|---|---|---|---|---|
| 2',5'-A-A-C | 35 | H | OH | OH | H | H |
| 2',5'-C-A-C | 36 | H | H | OH | H | N |
| 2',5'-A-A-Tu | 37 | H | OH | OH | OH | CH |
| 2',5'-A-A-A-3'-O-pentyl | 38 | H | OH | OH | O-n-C$_5$H$_{11}$ | N |
| 2',5'-A-A-A-3'-O-heptyl | 39 | H | OH | OH | O-n-C$_7$H$_{15}$ | N |
| 2',5'-A$_{(Si)}$-A$_{(Si)}$-A | 40 | H | OSiTBD | OSiTBD | OH | N |
| 2',5'-C-C-A | 41 | H | H | H | OH | N |
| 2',5'-A-C-C | 42 | H | OH | H | H | N |
| 2',5'-A-A-3'-amino | 43 | H | OH | OH | NH$_2$ | N |
| 2',5'-Trityl-A$_3$ | 44 | MMTr | OH | OH | OH | N |
| 2',5'-Trityl-C$_3$ | 45 | MMTr | H | H | H | N |
| 2',5'-C-C-C-5'-monophosphate | 46 | H$_2$O$_3$P | H | H | H | N |

EXAMPLE 2

Preparation of 3'-O-t-butyldimethylsilyladenylyl(2',5')3'-O-t-butyldimethylsilyladenylyl(2',5')adenosine 0.01 Mmole of N$^6$-benzoyl-3'-O-t-butyldimethylsilyl-5'-O-p-methoxytrityladenylyl(2'-o-chlorophenyl-5')N$^6$-benzoyl-3'-O-t-butyldimethylsilyladenylyl(2'-p-chlorophenyl-5')N$^6$, 2'-O,3'-O-tribenzoyladenosine (compound 31, Table 4) was treated according to the procedure of Example 1, except that the deprotection step of

EXAMPLE 5

Preparation of 5'-O-p-methoxytrityl-3'-deoxyadenylyl(2',5')3'-deoxyadenylyl(2',5')3'-deoxyadenosine 0.01 Mmole of N$^6$-benzoyl-5'-O-p-methoxytrityl-3'-deoxyadenylyl(2'-o-chlorophenyl-5')N$^6$-benzoyl-3'-deoxyadenylyl(2'-o-chlorophenyl-5')N$^6$,N$^6$,2'-O-tribenzoyl-3'-deoxyadenosine prepared according to the method of Charubala, R., and Pfleiderer, W., Tetrahedron Lett. 21, 4077

(1980) was treated according to the deprotection procedure of Example 1 except that the steps of treatment with tetrabutylammonium fluoride and acetic acid were omitted. The product, 2',5'-trityl-C$_3$ (compound 45, Table 5) was isolated, purified by DEAE-Sephadex A-25 chromatography and lyophilized to form the amorphous pure compound.

The 5'-monophosphates of the trimer core molecules of the present invention may be prepared from the fully blocked 2',5'-trinucleosidediphosphoditriester by detritylation as in Example 1 followed by reaction with di-p-nitrophenyl-ethylphosphoryl chloride. Extraction, chromatography and deblocking according to Example 1 results in isolation of the 5'-monophosphate trimers. The preparation is exemplified in the method of Example 6.

EXAMPLE 6

Preparation of 5'-O-phosphoryl-3'-deoxyadenylyl(2', 5')3'-deoxyadenylyl(2',5')3'-deoxyadenosine 0.1 Mmole of N$^6$-benzoyl-5'-O-p-methoxytrityl-3-deoxyadenylyl(2'-o-chlorophenyl-5')N$^6$-benzoyl-3'-deoxyadenylyl( 2'-o-chlorophenyl-5')N$^6$,N$^6$, 2'-Otribenzoyl-3'-deoxyadenosine is prepared from 3'-deoxyadenosine by benzoylation, 5'-tosylation, and 2'-phosphorylation, with formation of the dinucleoside phosphotriester, N$^6$-benzoyl (2-o-chlorophenylphosphoryl-5)3'-deoxyadenosine, by treatment of the reaction products N$^6$-benzoyl(2-triethylammonium-o-chlorophenylphosphoryl-5)-5'-tosyl-3'-deoxyadenosine and 2'-cyanoethylphosphoryl-o-chlorophenyl-3'-deoxyadenosine with triisopropylbenzenesulfonyl-nitro-1,2,4-triazolide. The fully blocked dimer thus formed is condensed with N$^6$, 2'-O-dibenzoyl-3'-deoxyadenosine to form the trimer. 0.01 mM of this trimer prepared according to the method of Charubala, R., and Pfleiderer, W., Tetrahedron Lett. 21, 4077 (1980) was treated with 2 ml of a solution of 2% p-toluenesulfonic acid in dichloromethane methanol (7/3, v/v) for 30 minutes at room temperature to remove the p-methoxytrityl group. Purification by silica gel chromatography on a preparative plate with chloroform/methanol (95/5, v/v) gave a 90% yield of the 5'-deprotected analog.

This product was dissolved in 1 ml of absolute pyridine and treated with 0.27 mmole of di-nitrophenylethylphosphoryl chloride as described by Himmelsbach, F., and Pfleiderer, W., Tetrahedron Lett. 23, 4973 (1982) for 1 hr. at room temperature. After dilution with 15 ml of chloroform, the reaction mixture was extracted three times with phosphate buffer pH 7. The organic layer was dried over sodium sulfate, filtered, evaporated and coevaporated three times with 10 ml of toluene each time. The residue was purified by silica gel chromatography on preparative plates in chloroform/methanol (9/1, v/v) to yield 81% of 5'-O-di-p-nitrophenylethylphosphoryl-N$^6$-benzoyl-3'-deoxyadenylyl-(2'-o-chlorophenyl-5')N$^6$-benzoyl-3'-deoxyadenylyl(2'-o-chlorophenyl-5')N$^6$,N$^6$, 2'-O-tribenzoyl-3'-deoxyadenosine in the form of an amorphous solid.

0.01 Mmole of the latter material was treated with o-nitrobenzaldoximate according to the deprotection procedure of Example 1 to remove o-chlorophenyl blocking groups. After evaporation to dryness and several coevaporations with absolute pyridine, the deprotected product was dissolved in 10 ml of a 0.5M solution of diazabicyclo[4.3.0] undecene in absolute pyridine and stirred for 36 hours at room temperature to cleave the p-nitrophenylethyl group by β-elimination. The solution was again evaporated and then treated with 20 ml of concentrated ammonium hydroxide for 24 hours at room temperature. Purification and isolation of the trimer core 5'-monophosphate (compound 46, Table 5) was achieved by DEAE-Sephadex chromatography and lyophilization of the main fraction.

The tetramer core molecules of the present invention may be prepared by following the method of Examples 7 or 8.

EXAMPLE 7

Preparation of Adenylyl(2',5')adenylyl(2',5')3'-deoxyadenylyl(2',5')3'-deoxyadenosine 0.5 Mmole of fully-protected compound 47 having the formula (VI) and 0.4 mmole of N$^6$-benzoyl-3'-deoxyadenylyl(2'-o-chlorophenyl-5')N$^6$, 2'-O-dibenzoyl-3'-deoxyadenosine (compound 24, Table 3) were dissolved in 5 ml of absolute pyridine.

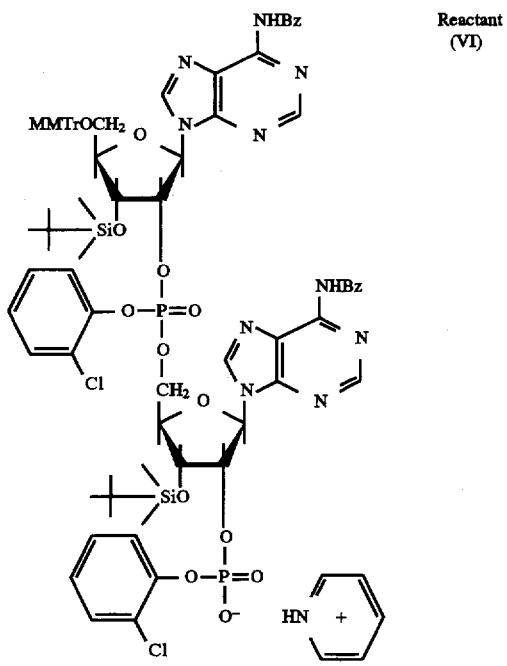

Following addition of 1 mmole of 2,4,6-triisopropylbenzenesulfonyl chloride and 3 mmole of 1-methylimidazone, the mixture was stirred for 2 hrs at room temperature. The solution was diluted with 400 ml of chloroform, washed twice with 400 ml of water, then the organic layer was dried over sodium sulfate, filtered and evaporated to dryness. The residue was coevaporated twice with 50 ml of toluene. Purification was achieved by chromatography on a silica gel column (20×2.5 cm) first with chloroform and then with a gradient of chloroform/methanol of 99/1 to 98/2 (v/v). On evaporation, the main fraction gave compound 48 (Table 6) as a solid foam in 80% yield. Compound 48 is a fully blocked 2',5'-tetranucleosidetriphosphotritriester according to the general formula of tetramer core (VII), below. Deprotection of the blocking groups was performed by the procedure of Example 1 to yield 2',5'-A-A-C-C (compound 49, Table 6). DEAE-Sephadex chromatography, evaporation and lyophilization resulted in an amorphous solid in 80% yield.

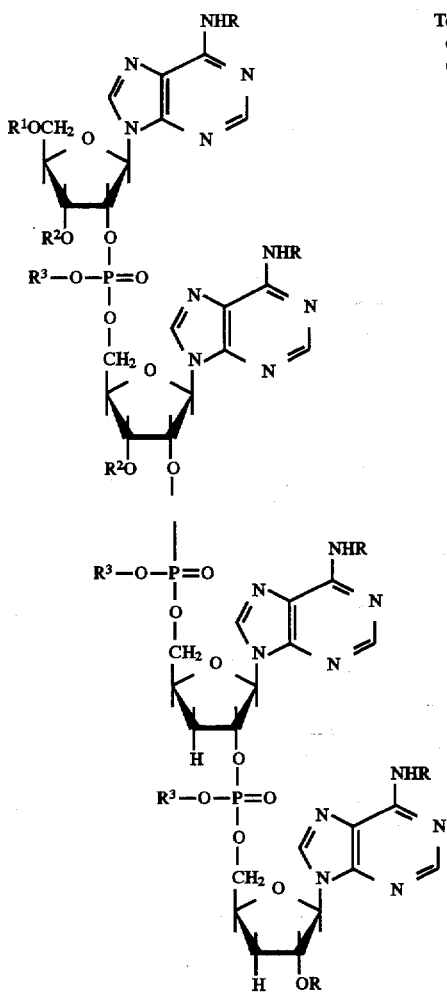

TABLE 6

| Compound No. | R | R¹ | R² | R³ |
|---|---|---|---|---|
| 48 | Bz | MMTr | SiTBD | 2-chlorophenyl |
| 49 | H | H | H | H |

EXAMPLE 8

Preparation of 3'-deoxyadenylyl(2',5')3'-deoxyadenylyl(2',5')3'-deoxyadenylyl(2',5')3'-deoxyadenosine 0.1 Mmole of $N^6$-benzoyl-5'-O-p-methoxytrityl-3'-deoxyadenylyl(2'-o-chlorophenyl-5')$N^6$-benzoyl-3,-deoxyadenylyl(2'-o-chlorophenyl-5')$N^6$, $N^6$, 2'-O-tribenzoyl-3'-deoxyadenosine (compound 50, Table 7), a fully-blocked 2',5'-trinucleosidediphosphoditriester according to the general formula of reactant (VIII),

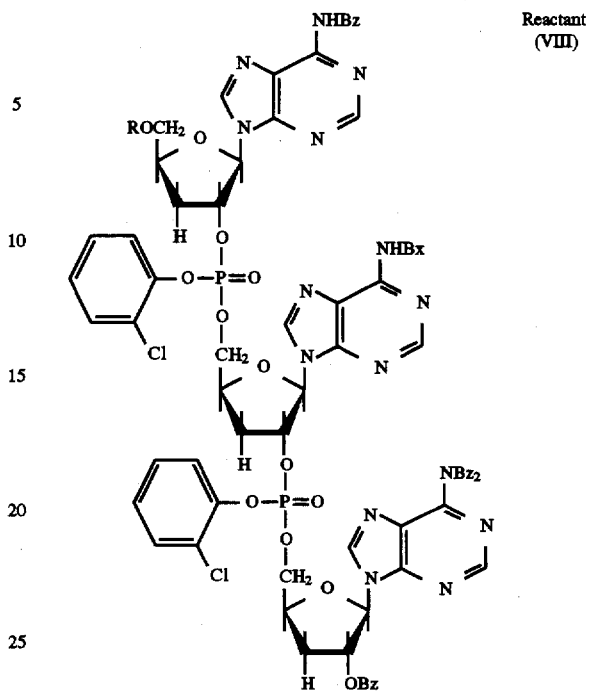

TABLE 7

| Compound No. | R |
|---|---|
| 50 | MMTr |
| 51 | H | was treated with 2 ml of a 2% solution of p-toluenesulfonic acid in dichloromethane/methanol (4/1, v/v) for 30 minutes at room temperature. The reaction was stopped by adding 20 ml of phosphate buffer pH 7. The solution was extracted several times with 200 ml of chloroform. The organic layer was washed with water, dried over sodium sulfate, filtered and evaporated to a small volume for purification on preparative silica gel plates in chloroform/methanol (95/5, v/v). The main band was eluted by chloroform/methanol (4/1, v/v) to give the 5'-detritylated compound 51 (Table 7) upon evaporation in 80% yield.

0.05 Mmole of compound 51 (Table 7) was then condensed with 0.1 mmole of pyridinium $N^6$-benzoyl-5'-O-p-methoxytrityl-3'-deoxyadenosine-2'-(2-o-chlorophenyl) phosphate (compound 2, Table 1) in 0.6 ml of absolute pyridine in the presence of 0.2 mmole of 2,4,6-triisopropylbenzene-sulfonyl chloride and 0.6 mmole of 1-methylimidazole for 2 hrs at room temperature. The solution was diluted with 100 ml of chloroform, washed twice with water, dried over sodium sulfate and evaporated to a small volume for separation on preparative silica gel plates in chloroform/methanol (95/5, v/v). The main band was eluted with chloroform to give the fully-protected 2',5'-tetranucleosidetriphosphotritriester compound 52 (Table 8, below) as an amorphous solid upon evaporation in 84% yield.

The blocking groups of compound 52 were removed according to the procedure of Example 1, followed by DEAE-Sephadex chromatography and lyophilization. Tetramer core 2',5'-C-C-C-C (compound 53, Table 8) resulted as an amorphous solid in 70% yield. The structure of compound 53 is according to the general formula of tetramer core (IX).

The 5'-O-monophosphates of the tetramer core molecules of the present invention may be prepared from the fully blocked 2',5'-tetranucleosidetriphosphotritriester by 5'-detritylation as in Example 1 followed by reaction with di-p-nitrophenylethylphosphoryl chloride. Extraction, chromatography and deblocking according to Example 1 results in isolation of the 5'-O-monophosphate tetramers. The preparation is exemplified in Example 6, above.

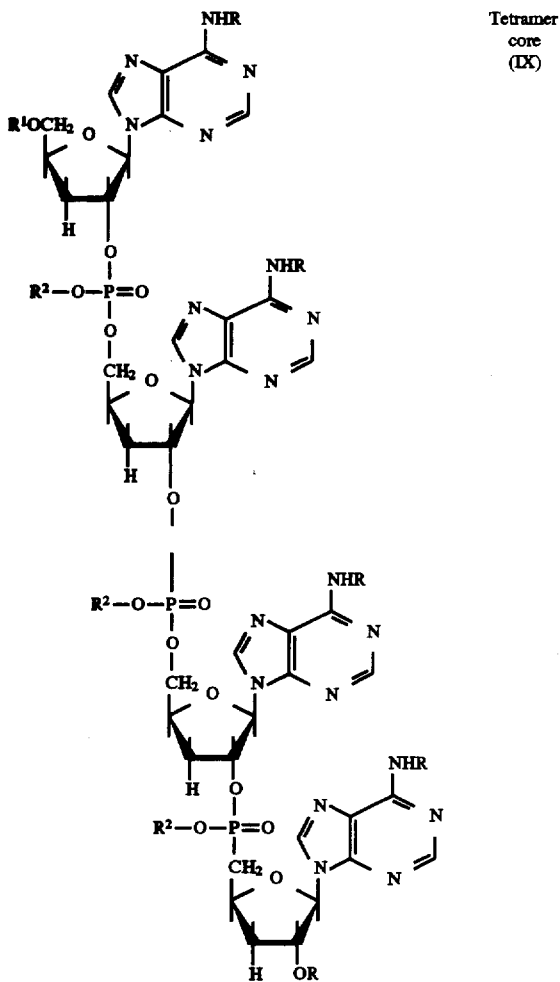

Tetramer core (IX)

TABLE 8

| Compound No. | R | R¹ | R² |
|---|---|---|---|
| 52 | Bz | MMTr | 2-chlorophenyl |
| 53 | H | H | H |

The 5'-diphosphate and 5'-triphosphate of the trimer and tetramer core molecules of the present invention may be prepared by adding 0.5 mM of tributylammonium pyrophosphate dissolved in 5 ml of dimethylformamide to 0.1 mM of monophosphorylated core as the anhydrous tributylammonium salt in 1 ml of dimethylformamide and 0.5 mM of 1,1'-carbonyldiimidazole. After 20 hours at room temperature, the reactants are treated with 5 ml of methanol, evaporated to dryness and chromatographed on a 2×20 cm DEAE cellulose column. The 5'-di and triphosphates are isolated following a linear gradient (0–0.4M in 3 1 at pH 7.5) of triethylammoniumbicarbonate. This is the method of Hoard, D. E., and Ott, D. G., J. Amer. Chem. Soc. 87, 1785–1788 (1965), which is incorporated herein by reference. The 5'-diphosphates and 5'-triphosphates may then be purified by DEAE-Sephadex A25 and Sephadex G-10 chromatography.

Structural modification of the 2',5'-oligoadenylate molecule at the 2'-terminal nucleoside, aglycon and/or ribosyl moiety have provided molecules that are potent inhibitors of virus replication, particularly replication of retroviruses, such as HIV. These synthetic molecules are biologically more active and metabolically more stable than the naturally occurring 2',5'-oligoadenylate molecule.

The antiretroviral activity of the compounds of the present invention is demonstrated by the following experimental methods in which any of the core compounds of the invention or their 5' mono, -di-, or triphosphate counterparts may be substituted for any of the analogs in the following experiments with the efficacy disclosed for such compounds in the specification.

According to the following experiment, the 2',5'-oligoadenylate analogs were observed to inhibit HIV-1 reverse transcriptase activity and protect target cells from HIV-1 infection in vitro.

EXAMPLE 9

Inhibition of HIV-1 Reverse Transcriptase Activity In Vitro

Cells and Virus. Cells of highly HIV-1 permissive T-cell line MT-2 (Miyoshi et al., Nature 294:770–771 (1981)) were used as target cells for infection while with HIV-1 (HTLV-III$_B$) produced in H9 cells (Popovic et al., Science 224: 497–500 (1984)). Stock cultures were grown and maintained in RPMI-1640 containing 12% heat inactivated fetal bovine serum and 50 microgram gentamicin/ml and incubated at 37° C. Viral titers in this study, which are given as a multiplicity of infection (i.e., infectious virus particles/cell), were calculated from 50% tissue culture infectious dose values obtained by end-point microtitration on MT-2 cells as described in Montefiori et al., J. Clin. Microbiol. 26: 231–235 (1987).

Reverse Transcriptase Assays. Virus was concentrated from cell-free (0.45 micromolar-filtered) conditioned H9/HTLV-III$_B$ culture supernatants by centrifugation at 18,000 r.p.m. for 4 hrs at 20° C. in a Beckman JA-20 rotor. A viral pellet obtained from 50 ml of conditioned culture fluid was dissolved in 0.5 mL of a solution containing 17 mM Tris-HCl (pH 7.8), 3mM dithiothreitol (DTT), 55 mM KCl, 0.32% w/v Triton X-100, and 33% glycerol. This viral lysate was stored at −20° C. and was used as a source of HIV-1 reverse transcriptase. Reverse transcriptase reactions were performed in 100 uL reaction volumes containing 40 mM Tris-HCl (pH 7.8), 4 mM DTT, 50 mM KCl, 10 mM MgCl$_2$, 0.0325% w/v Triton X-100, 3 micromolar [$^3$H] dTTP (80 Ci/mmol,NEN) and poly (A).(dT)$_{15}$(2.5 microgram/mL) template-primer after the addition of 10 microliter enzyme. Inhibitors were added at various concentrations after adjusting water volumes so that reaction volumes remained constant. Reactions were incubated at 37° C. for 1 hr in a humidified environment and terminated by adding 2 mL of 10% cold trichloroacetic acid. Precipitate was collected on 0.45 micron cellulose-acetate Millipore filters which were then dissolved in 10 mL of 3a70B aqueous scintillant and the counts per minute quantitated using a Beckman LS 6800 liquid scintillation spectrometer.

Infection Assays. Anti-HIV-1 activities of various compounds were detected and quantitated by an in vitro microtiter infection assay as previously described by Montefiori, supra. Briefly, MT-2 cells were added to 96-well microdilution plates containing 2-fold serial dilutions of effector in triplicate. Virus was added at a multiplicity of infection of 1 and the plates incubated at 37° C. in a humidified 5% $CO_2$/air environment for 4 days. Viable cells were then quantitated by vital dye (neutral red) uptake of poly-L-lysine adherent cells as a measure of cytopathic effect. At this time, virus control wells (cells and virus in the absence of effectors) exhibited greater than 90% cytolysis. Percent protection was defined by the range of $A_{540}$ readings occurring between cell control wells (cells in the absence of virus and effectors) and virus control wells.

Cell Toxicity Assays. Cell toxicities were quantitated using MT-2 cells in microdilution plates as described above with the exceptions of omitting virus and replacing virus control wells with empty (blank) wells. The range of $A_{540}$ readings occurring between cell control wells and blank wells was used to calculate percent viable cells in test wells after 3 days incubation.

The effects of analogues of 2–5A on HIV-1 reverse transcriptase activity are shown in Table 9 and in FIG. 1. Concentration-dependent inhibition of enzyme activity was observed, for instance, with 2',5'-cordycepin trimer core ($C_3$), trimer 5'-mono-, di and triphosphates ($pC_3$, $p_2C_3$, $p_3C_3$), 2',5'-cordycepin tetramer 5'-monophosphate ($pC_4$), in addition to 2',5'-A-C-A. (FIG. 1) The 5,6-dichlorobenzimidazole riboside 2',5'-trimer was the most effective inhibitor (73% inhibition at 200 micromolar), followed by 2',5'-$pC_4$ (64% inhibition at 200 micromolar), followed by the 2',5'-cordycepin trimer 5'-triphosphate ($p_3C_3$) (62% at 200 micromolar), 2',5'-A-C-A (58% inhibition at 200 micromolar) and 2',5'-A-A-ara-A (53% inhibition at 200 micromolar). (Table 9)

TABLE 9

Effect of 2-5A Analogues on HIV-1 Reverse Transcriptase Activity

| 2-5A or 2',5' Analogue | Concentration (micromolar) | Percent Inhibition[a] |
|---|---|---|
| (adenosine) A | 400 | 0 |
| $A_3$ | 200 | 0 |
| $pA_3$ | 200 | 29 |
| $p_3A_3$ | 200 | 0 |
| cordycepin (C) | 400 | 0 |
| $C_3$ | 200 | 31 |
| $pC_3$ | 200 | 43 |
| $p_3C_3$ | 200 | 62 |
| $C_4$ | 200 | 39 |
| $pC_4$ | 200 | 64 |
| A-C-C | 200 | 42 |
| A-A-C | 200 | 16 |
| C-A-C | 200 | 36[b] |
| A-C-A | 200 | 58 |
| A-A-C-C | 200 | 35[b] |
| A-A-C-A | 200 | 7 |
| $pI_3$ | 200 | 35 |
| A-A-ara-A | 200 | 53 |
| Tu-Tu-Tu | 200 | 41 |
| xylo-$A_4$ | 200 | 15 |
| A-A-A-3'-amino | 200 | 43 |
| EHNA-A-A | 200 | 36 |
| 5,6-dichlorobenzimidazylyl)2'-5')-5,6-dichlorobenzimidazylyl-(2',5')-5,6-dichlorobenzimidazole riboside | 200 | 73 |

[a]Values for control reactions (i.e. no inhibitor present) were greater than 180,000 cpm while blank reaction (no enzyme present) values were less than 12,000 cpm.
[b]Average of two or more experiments.

Results of infection assays with certain of the 2–5A analogues are shown in FIG. 2. Referring to FIG. 2, concentration-dependent anti-HIV-1 activity was observed for 2',5'-cordycepin trimer core (I) and 5'-monophosphate (IV) at exogenous concentrations of 8–250 micromolar, and for 2',5'-A-C-A (V) at 1–8 micromolar. These activities were 84%, 80% and 81%, respectively, of the optimum anti-HIV-1 activity provided by mismatched dsRNA (data not shown). This is quite significant anti-HIV activity considering that mismatched dsRNA is a potent anti-HIV drug in vitro. Montefiori et al., Proc. Natl. Acad. Sci. USA 84: 2985–2989 (1987). Less potent concentration- dependent anti-HIV-1 activity was observed for 2',5'-$pC_4$ (VI) at 12.5–50 micromolar. No cell toxicity was observed for $C_3$ and A-C-A at the most effective concentrations, while mild toxicity was observed for $pC_3$ and $pC_4$ at some of these optimal antiviral concentrations.

In contrast, cordycepin (I) (0.31–10 micromolar) and 2',5'-oligoadenylate trimer core (II) (8–250 micromolar) demonstrated no antiviral activity. Cell toxicity was observed at exogenous concentrations greater than 2.5 micromolar for cordycepin while no toxicity was observed at any concentrations of 2',5'-oligoadenylate trimer core tested. The 2',5'-cordycepin tetramer 5'-monophosphate (VI) demonstrated weak anti-HIV-1 activity in vitro (30–38% protection of exogenous concentrations of 12.5 to 50 micromolar) while concentrations greater than 50 micromolar were toxic to the cells (data not shown).

In the same infection assay, 2',5'-xylo-$A_4$ provided 100% inhibition at 150 micromolar concentration (91% at 75 micromolar), while 2',5'-A-A-A-3'-amino provided 100% inhibition at 75 micromolar. No toxicity was observed at these dosages.

When combined with other drugs, the 2–5A analogs may exhibit synergism with respect to anti-HIV activity, as demonstrated in the following experiment.

EXAMPLE 10

Figure 3A:
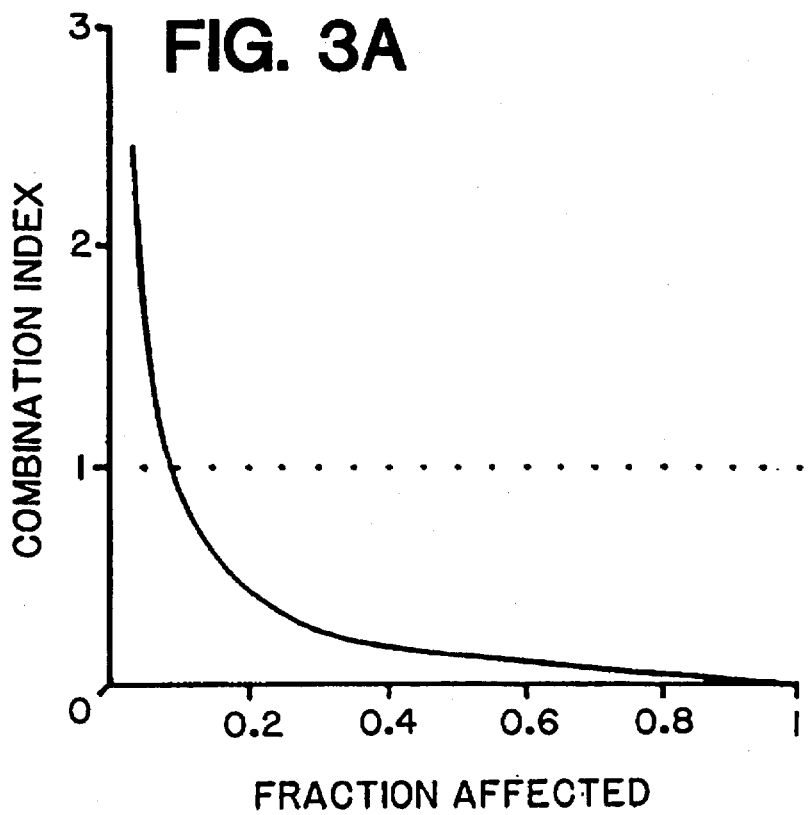
FIG. 3 is a plot of the combined anti-HIV-1 effect of 2',5'-$C_3$ with either rIFN-αA (3A), or mismatched dsRNA (3B). A combination drug index was calculated from the slopes of dose-effect curves and plotted against the percent protection values, or fraction affected. Concentrations were 3.1–100 μg/ml for 2',5'-$C_3$, 9.8–312.5 I.U./ml for rIFN-αA and 1.6–25 μg/ml for mismatched dsRNA.
Figure 3B:
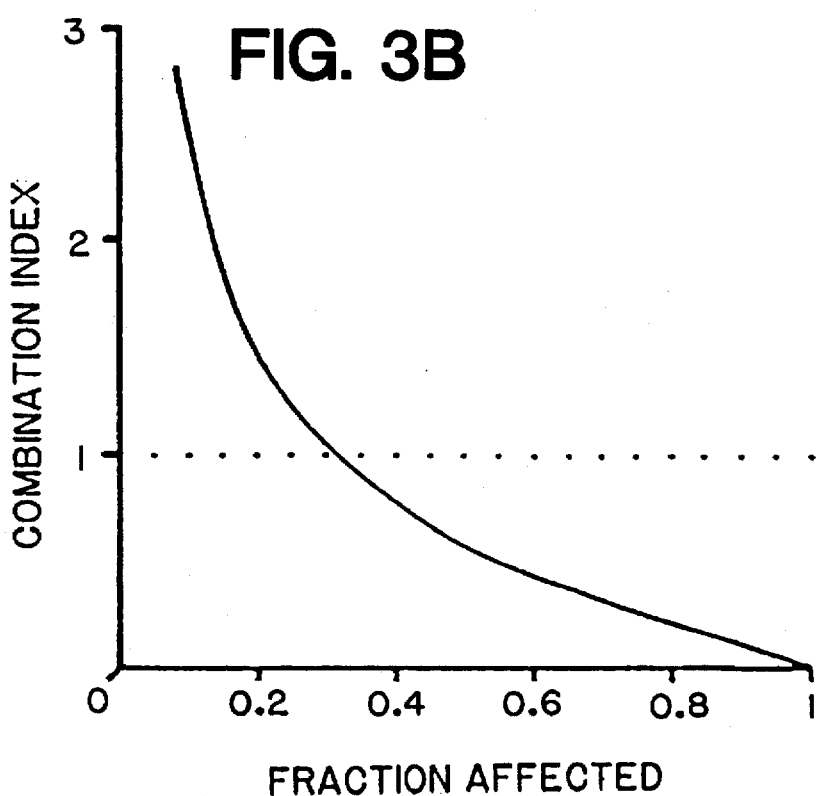

The ability of 2',5'-$C_3$ to potentiate or abrogate the in vitro antiviral activities of recombinant α-interferon (rIFN-αA) and a mismatched dsRNA inducer of interferon was tested. A standard checkerboard analysis was performed at 8 non-toxic concentrations of each drug alone and in combination. The data was analyzed by the method of Chou and Talay, Adv. Enzyme Regul. 22:27–55 (1984). Briefly, combined drug effects were calculated from percent protection values. A combination index (CI) was calculated from the slopes of dose-effect curves and plotted against the percent protection values, or fraction affected. CI values of <1 indicate synergy. Values >1 indicate antagonism. Values equal to 1 indicate additiveness. The results are shown in FIG. 3. The 2',5'-cordycepin trimer core demonstrated strong synergism with both rIFN-αA and mismatched dsRNA at the most effective doses of each drug tested. Synergism was stronger for rIFN-αA than for mismatched dsRNA.

All references herein cited with respect to synthetic or analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method of treating a mammal for retroviral infection comprising administering to a mammal in need of such treatment a compound of the formula

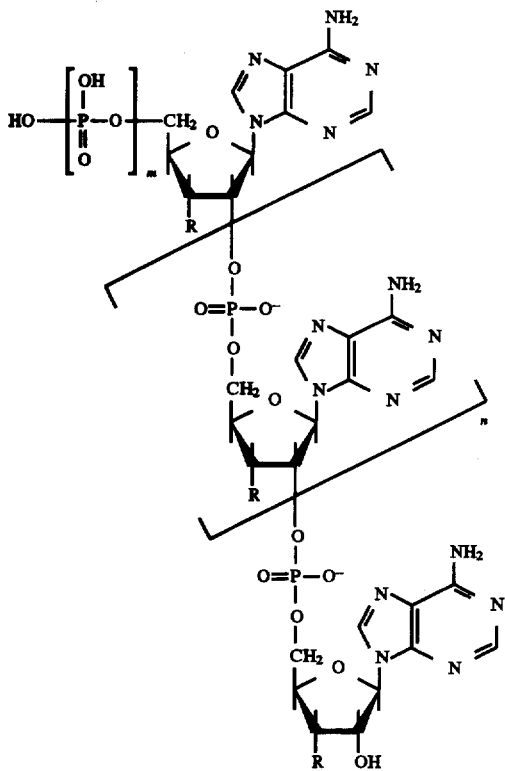

wherein n is a number from 1 to 8 m is 0, 1, 2, or 3, and

R, same or different, is selected from hydrogen, hydroxy, amino, $C_1$-$C_{10}$-alkoxy and —$OSi(CH_3)_2C(CH_3)_3$, provided that all R groups may not be hydroxy in the same compound, or pharmaceutically acceptable salts thereof.

2. A method according to claim 1 wherein n is from 1 to 3.

3. A method according to claim 2 wherein the R group of the 2'-terminal nucleotide is other than hydroxy.

4. A method according to claim 1 for the treatment of HIV infection.

5. A method according to claim 2 wherein each R, the same or different, is selected from hydrogen and hydroxy.

6. A method according to claim 4 wherein each R, the same or different, is selected from hydroxy and amino.

7. A method according to claim 5 wherein the compound is selected from the group of 3'-deoxyadenylyl-(2',5')3'-deoxyadenylyl(2',5')3'-deoxyadenosine, the 5' mono-, di- and triphosphates thereof, and pharmaceutically acceptable salts of any of them.

8. A method according to claim 7 wherein the compound is the 5'-triphosphate or pharmaceutically acceptable salt thereof.

9. A method according to claim 5 wherein the compound is selected from the group of 3'-deoxyadenylyl-(2',5')3'-deoxyadenylyl(2',5')3'-deoxyadenylyl(2',5')3'-deoxyadenosine, the 5' mono-, di- and triphosphates thereof, and pharmaceutically acceptable salts of any of them.

10. A method according to claim 5 wherein the compound is selected from the group of adenylyl(2',5')3'-deoxyadenylyl(2',5')3'-deoxyadenosine, the 5' mono-, di- and triphosphates thereof, and pharmaceutically acceptable salts of any of them.

11. A method according to claim 5 wherein the compound is selected from the group of adenylyl(2',5')-adenylyl(2',5') 3'-deoxyadenosine, the 5' mono-, di- and triphosphates thereof, and pharmaceutically acceptable salts of any of them.

12. A method according to claim 5 wherein the compound is selected from the group of 3'-deoxyadenylyl(2',5') adenylyl(2',5')3'-deoxyadenosine, the 5' mono-, di- and triphosphates thereof, and pharmaceutically acceptable salts of any of them.

13. A method according to claim 5 wherein the compound is selected from the group of adenylyl(2',5')3'-deoxyadenylyl(2',5') adenosine, the 5' mono-, di- , and triphosphates thereof, and pharmaceutically acceptable salts of any of them.

14. A method according to claim 13 wherein the compound is adenylyl(2',5')3'-deoxyadenylyl-(2',5')adenosine, or pharmaceutically acceptable salt thereof.

15. A method according to claim 5 wherein the compound is selected from the group of adenylyl(2',5')adenylyl(2',5') 3'-deoxyadenylyl(2',5')3'-deoxyadenosine, the 5' mono-, di- and triphosphates thereof, and pharmaceutically acceptable salts of any of them.

16. A method according to claim 5 wherein the compound is selected from the group of adenylyl(2',5')adenylyl(2',5') 3'-deoxyadenylyl(2',5')adenosine, the 5' mono-, di- and triphosphates thereof, and pharmaceutically acceptable salts of any of them.

17. A method according to claim 6 wherein the compound is selected from the group of adenylyl(2',5')adenylyl(2',5') 3'-amino-3'-deoxyadenosine, the 5' mono-, di- and triphosphates thereof, and pharmaceutically acceptable salts of any of them.

18. A method according to claim 17 wherein the compound is adenylyl(2',5')adenylyl(2',5')3'-amino-3'-deoxyadenosine or a pharmaceutically acceptable salt thereof.

19. A method according to claim 2 wherein each R is hydrogen.

20. A method according to claim 1 for the treatment of chronic virus infection.

21. A method according to claim 1 for the treatment of hepatitis infection.

22. A method according to claim 5 wherein the compound is selected from the group of 3'-deoxyadenylyl(2',5')-3'-deoxyadenylyl(2',5')adenosine, the 5' mono-, di- and triphosphates thereof, and pharmaceutically acceptable salts of any of them.

23. A method of treating a mammal for retroviral infection comprising administering to a mammal in need of such treatment a compound selected from the group of the following compounds, or the 5'mono-, di-, or triphosphates thereof, or a pharmaceutically acceptable salt of any of them:

3'-deoxyadenylyl(2',5')3'-deoxyadenylyl-(2',5')-(R)-3-(2-deoxy-β-erythropentofuranosyl)-3,6,7,8-tetrahydroimidaxo[4,5,-d][1,3]diazepine-8-ol, adenylyl(2',5')adenylyl(2',5')tubercidin, tubercidylyl(2',5')tubercidylyl(2',5')tubercidin, adenylyl(2',5')adenylyl(2',5')9-β-D-arabinofuranosyladenine, inosinylyl(2',5')inosinylyl(2',5')inosine, xyloadenylyl(2',5')xyloadenylyl(2',5')xyloadenylyl(2',5') xyloadenosine, erythro-9(2-hydroxy-3-nonyl)adenylyl-(2',5')-adenylyl-(2',5')adenosine, 5,6-dichlorobenzimidazylyl(2',5')5,6-dichlorobenzimidazylyl(2',5')5,6-dichlorobenzimidazole.

24. A method according to claim 23 wherein the compound is adenylyl(2',5')adenylyl(2',5')tubercidin, the 5' mono-, di-, or triphosphate thereof, or a pharmaceutically acceptable salt of any of them.

25. A method according to claim 23 wherein the compound is adenylyl(2',5')adenylyl(2',5')9-β-D-arabinofuranosyladenine, the 5' mono-, di-, or triphosphate thereof, or a pharmaceutically acceptable salt of any of them.

26. A method according to claim 23 wherein the compound is inosinylyl(2',5')inosinylyl(2',5')inosine, the 5' mono-, di-, or triphosphate thereof, or a pharmaceutically acceptable salt of any of them.

27. A method according to claim 23 wherein the compound is xyloadenylyl(2',5')xyloadenylyl(2',5')xyloadenosine, the 5' mono-, di-, or triphosphate thereof, or a pharmaceutically acceptable salt of any of them.

28. A method according to claim 23 wherein the compound is xyloadenylyl(2',5')xyloadenylyl(2',5')xyloadenylyl(2',5')xyloadenosine, the 5' mono-, di-, or triphosphate thereof, or a pharmaceutically acceptable salt of any of them.

29. A method according to claim 23 wherein the compound is tubercidylyl(2',5')tubercidylyl(2',5')tubercidin, the 5' mono-, di-, or triphosphate thereof, or a pharmaceutically acceptable salt of any of them.

30. A method according to claim 23 wherein the compound is erythro-9(2-hydroxy-3-nonyl)adenylyl(2',5')adenylyl(2',5')adenosine, the 5' mono-, di-, or triphosphate thereof, or a pharmaceutically acceptable salt of any of them.

31. A method according to claim 23 wherein the compound is 5,6-dichlorobenzimidazylyl(2',5')5,6-dichlorobenzimidazylyl(2',5')5,6-dichlorobenzimidazole riboside, the 5' mono-, di-, or triphosphate thereof, or a pharmaceutically acceptable salt of any of them.

32. A method according to claim 23 for the treatment of HIV infection.

33. A method according to claim 23 wherein the compound is 3'-deoxyadenylyl(2',5')3'-deoxyadenylyl(2',5')-(R)-3-(2-deoxy-β-D-erythropentofuranosyl)-3,6,7,8-tetrahydroimidazo[4,5,-d][1,3]diazepine-8-ol, the 5' mono-, di-, or triphosphate thereof, or a pharmaceutically acceptable salt of any of them.

34. A method according to claim 23 for the treatment of chronic virus infection.

35. A method according to claim 23 for the treatment of hepatitis infection.

36. Erythro-9(2-hydroxy-3-nonyl)adenylyl-(2',5')adenylyl(2',5')adenosine, the 5' mono, di-, or triphosphate thereof, or a pharmaceutically acceptable salt of any of them.

37. 5,6-Dichlorobenzimidazylyl(2',5')5,6-dichlorobenzimidazylyl(2',5')5,6-dichlorobenzimidazole riboside, the 5' mono, di-, or triphosphate thereof, or a pharmaceutically acceptable salt of any of them.

* * * * *